United States Patent
Sugiyama et al.

(10) Patent No.: US 8,603,997 B2
(45) Date of Patent: Dec. 10, 2013

(54) SIRNA THAT INHIBITS WT1 GENE EXPRESSION AND USES THEREOF

(71) Applicant: Haruo Sugiyama, Osaka (JP)

(72) Inventors: Haruo Sugiyama, Osaka (JP); Yusuke Oji, Osaka (JP)

(73) Assignee: Haruo Sugiyama, Osaka (JP)

( * ) Notice: Subject to any disclaimer, the term of this patent is extended or adjusted under 35 U.S.C. 154(b) by 0 days.

(21) Appl. No.: 13/659,450

(22) Filed: Oct. 24, 2012

(65) Prior Publication Data

US 2013/0115696 A1 May 9, 2013

Related U.S. Application Data

(63) Continuation of application No. 10/594,939, filed as application No. PCT/JP2005/005824 on Mar. 29, 2005, now Pat. No. 8,299,234.

(30) Foreign Application Priority Data

Mar. 29, 2004 (JP) ................................. 2004-096876

(51) Int. Cl.
- *C12N 15/11* (2006.01)
- *A61K 48/00* (2006.01)
- *C07H 21/02* (2006.01)
- *C07H 21/04* (2006.01)

(52) U.S. Cl.
USPC ........................................ 514/44 A; 536/24.5

(58) Field of Classification Search
USPC .......................................... 514/44; 536/24.5
See application file for complete search history.

(56) References Cited

U.S. PATENT DOCUMENTS

| | | | |
|---|---|---|---|
| 6,034,235 | A | 3/2000 | Sugiyama et al. |
| 6,225,051 | B1 | 5/2001 | Sugiyama et al. |
| 6,232,073 | B1 | 5/2001 | Ware et al. |
| 6,277,832 | B1 | 8/2001 | Sugiyama et al. |
| 8,299,234 | B2 | 10/2012 | Sugiyama et al. |
| 2003/0092656 | A1 | 5/2003 | Sugiyama |
| 2004/0043950 | A1 | 3/2004 | Lopez-Berestein et al. |
| 2005/0118625 | A1 | 6/2005 | Mounts |
| 2006/0105981 | A1 | 5/2006 | Sugiyama |
| 2007/0287175 | A1 | 12/2007 | Sugiyama et al. |
| 2008/0003637 | A1 | 1/2008 | Sugiyama et al. |
| 2008/0038819 | A1 | 2/2008 | Sugiyama et al. |

FOREIGN PATENT DOCUMENTS

| | | |
|---|---|---|
| EP | 0841068 | 5/1998 |
| EP | 1004319 | 5/2000 |
| EP | 1738771 | 1/2007 |
| JP | 09-104629 | 4/1997 |
| WO | WO 96/38176 | 12/1996 |
| WO | WO 99/03506 | 1/1999 |
| WO | WO 03/061386 | 7/2003 |

(Continued)

OTHER PUBLICATIONS

Arai et al., "Mesenchymal stem cells in perichondrium express activated leukocyte cell adhesion molecule and participate in bone marrow formation," J. Exp. Med. 195(12):1549-1563, 2002.

(Continued)

*Primary Examiner* — Terra Cotta Gibbs
(74) *Attorney, Agent, or Firm* — Fish & Richardson P.C.

(57) ABSTRACT

The present inventors discovered that siRNAs targeting the 17AA site of the WT1 gene not only suppress the expression of the WT1 gene, but also demonstrate remarkable cell growth-suppressing effects and cell death-inducing effects in cancer cell lines.

40 Claims, 18 Drawing Sheets

(56) References Cited

FOREIGN PATENT DOCUMENTS

| WO | WO 2005/092393 | 6/2005 |
|---|---|---|
| WO | WO 2005/092394 | 6/2005 |
| WO | WO 2005/093076 | 6/2005 |

OTHER PUBLICATIONS

Asahara et al., "Isolation of putative progenitor endothelial cells for angiogenesis," Science 275:964-967, 1997.
Ast et al., "Antisense oligonucleotide binding to U5 snRNP induces a conformational change that exposes the conserved loop of U5 snRNA," Nucleic Acids Research, 25(17):3508-3513, 1997.
Baird et al., "Expression of the Wilms' tumor gene (WT1) in normal hemopoiesis," Exp. Hematol., 25:312-320, 1997.
Borkhardt et al., "Blocking oncogenes in malignant cells by RNA interference—new hope for a highly specific cancer treatment?," 2(3):167-168, 2002.
Call et al., "Isolation and characterization of a zinc finger polypeptide gene at the human chromosome 11 Wilms' tumor locus," Cell 60:509-520, 1990.
Davies et al., "Development of an siRNA-based method for repressing specific genes in renal organ culture and its use to show that the WT1 tumor suppressor is required for nephron differentiation," Human Molecular Genetics 13(2):235-246, 2004.
Ellisen et al., "The Wilms' tumor suppressor WT1 directs stage-specific quiescence and differentiation of human hematopoietic progenitor cells," EMBO J., 20:1897-1909, 2001.
Elmaagacli et al., "WT1 and BCR-ABL specific small interfering RNA have additive effects in the induction of apoptosis in leukemic cells," Haematologica 90(3):326-334, 2005.
Fiering et al., "Improved FASC-Gal: Flow cytometric analysis and sorting of viable eukaryotic cells expressing reporter gene constructs," Cytometry 12:291-301, 1991.
Gessler et al., "Homozygous deletion in Wilms tumours of a zinc-finger gene identified by chromosome jumping," Nature 343:774-778, 1990.
Gordon et al., "Temporal Analysis of Hepatocyte Differentiation by Small Hepatocyte-Like Progenitor Cells during Liver Regeneration in Retrorsine-Exposed Rats," Am. J. Pathol., 157:771-786, 2000.
Hammond et al., "Post-Transcriptional Gene Silencing by Double-Stranded RNA," Nature Genetics, 2:110-119, 2001.
Hosen et al., "Very low frequencies of human normal $CD34_+$ hematopoietic progenitor cells express the Wilms' tumour gene WT1 at levels similar to those in leukaemia cells," Br. J. Haeomatol. 116(2):409-420, 2002.
Hübinger et al., "Ribozyme-mediated cleavage of wt1 transcripts suppresses growth of leukemia cells," Experimental Hematology 29:1226-1235, 2001.
Inoue et al., "Aberrant Overexpression of the Wilms' Tumor Gene (WT1) in Human Leukemia," Blood, 89:1405-1412, 1997.
Inoue et al., "Wilms' tumor gene (WT1) competes with differentiation-inducing signal in hematopoietic progenitor cells," Blood 91(8):2969-2976, 1998.
Inoue et al., "WT1 as a new prognostic factor and a new marker for the detection of minimal residual disease in acute leukemia," Blood 84(9):3071-3079, 1994.
Jin et al., "Polypyrimidine Tract-Binding Protein Down-Regulates Fibroblast Growth Factor Receptor 1 alpha-Exon Inclusion," Cancer Research, 63:6154-6157, 2003.
Kanato et al., "The Wilms' tumor gene WT1 is a common marker of progenitor cells in fetal liver," Biochem. Biopys. Res. Commun. 326:836-843, 2005.
Kawasaki et al., "New current of non-coding RNA's: new gene expression control by microRNA's," Jikken Igaku 22(4):492-499, 2004 (with English translation).
Kreidberg et al., "WT-1 is required for early kidney development," Cell 74:679-691, 1993.
Larsson et al., "Subnuclear localization of WT1 in splicing or transcription factor domains is regulated by alternative splicing," Cell 81:391-401, 1995.

Li et al., "The lck Promoter-Driven Expression of the Wilms' Tumor Gene WT1 Blocks Intrathymic Differentiation of T-Lineage Cells," Int. J. Hematol., 77:463-470, 2003.
Loeb et al., "The role of WT1 in oncogenesis: tumor suppressor or oncogene?" International Journal of Hematology 76:117-126, 2002.
Mallardo et al., "Microtubule-dependent Organization of Vaccinia Virus Core-derived Early mRNAs into Distinct Cytoplasmic Structures," Molecular Biology of the Cell, 12:3875-3891, 2001.
McManus et al., "Small Interfering RNA-Mediated Gene Silencing in T Lymphocytes," J. Immunol., 169:5754-5760, 2002.
McManus, "MicroRNAs and cancer," Seminars in Cancer Biology, 13:253-258, 2003.
Menke et al., "The Wilms' tumor 1 gene: oncogene or tumor suppressor gene?," Int. Rev. Cytol. 181:151-212, 1998.
Menssen et al., "Wilms' tumor gene (WT1) expression as a panleukemic marker," Int. J. Hematol. 76(2):103-109, 2002.
Menssen et al., "Wilms' tumor gene (WT1) expression as a panleukemic marker," Blood 89(9):3486-3487, 1997.
Moore et al., "YAC transgenic analysis reveals Wilms' Tumour 1 gene activity in the proliferating coelomic epithelium, developing diaphragm and limb," Mechanisms of Development 79:169-184, 1998.
Morrison et al., "A proteomic investigation of the role of WT-1 in disease," Biochemical Society Transactions 32(4):116A, 2004.
Morrison et al., "The biology of hematopoietic stem cells," Annu. Rev. Cell Dev. Biol. 11:35-71, 1995.
Mourellatos et al., "miRNPs: a novel class of ribonucleoproteins containing numerous microRNAs," Genes Dev. 16(6):720-728, 2002.
Murata et al., "The Wilms' tumor suppressor gene WT1 induces G1 arrest and apoptosis in myeloblastic leukemia M1 cells," FEBS Letters 409(1):41-45, 1997.
Murayama et al., "Flow cytometric analysis of neural stem cells in the developing and adult mouse brain," Journal of Neuroscience Research 69:837-847, 2002.
Oji et al., "Absence of mutations in the Wilms' tumor gene wtl in de novo non-small cell lung cancers," Neoplasma 51(1):17-20, 2004.
Oji et al., "Absence of mutations in the Wilms' tumor gene WT1 in primary breast cancer," Jpn. J. Clin. Oncol. 34(2):74-77, 2004.
Oji et al., "Expression of the Wilms' tumor gene WT1 in solid tumors and its involvement in tumor cell growth," Japanese Journal of Cancer Research 90:194-204, 1999.
Oji et al., "Overexpression of the Wilms' tumor gene WT1 in colorectoral adenocarcinoma," Cancer Science 94(8):712-717, 2003.
Oji et al., "Overexpression of the Wilms' tumor gene WT1 in de novo lung cancers," Intl. J. Cancer 100:297-303, 2002.
Oji et al., "Overexpression of the Wilms' tumor gene WT1 in esophageal cancer," Anticancer Research 24:3103-3108, 2004.
Oji et al., "Overexpression of the Wilms' tumor gene WT1 in head and neck squamous cell carcinoma," Cancer Science 94(8):523-529, 2003.
Oji et al., "Overexpression of the Wilms' tumor gene WT1 in pancreatic ductal adenocarcinoma," Cancer Science 95(7):583-587, 2004.
Oji et al., "Overexpression of the Wilms' tumor gene WT1 in primary thyroid cancer," Cancer Science 94(7):606-611, 2003.
Oji et al., "Overexpression of the Wilms' tumor gene WT1 in primary astrocytic tumors," Cancer Science 95(10):822-827, 2004.
Roy et al., "In vitro neurogenesis by progenitor cells isolated from the adult human hippocampus," Nature Medicine 6(3):271-277, 2000.
Sugiyama, "Wilms' tumor gene WT1: Its oncogenic function and clinical application," Int. J. Hematol. 73:177-187, 2001.
Suzuki et al., "Flow-cytometric separation and enrichment of hepatic progenitor cells in the developing mouse liver," Hepatology 32:1230-1239, 2000.
Trayhurn, "Northern blotting," Proc. Nutr. Soc., 55:583-589 (1996).
Ueda et al., "Overexpression of the Wilms' tumor gene WT1 in human bone and soft-tissue sarcomas," Cancer Science 94(3):271-276, 2003.
Vickers et al., "Efficient Reduction of Target RNAs by Small Interfering RNA and RNase H-dependent Antisense Agents," The Journal of Biological Chemistry, 278(9):7108-7118, 2003.

(56) References Cited

OTHER PUBLICATIONS

Yamagami et al., "Growth inhibition of human leukaemic cells by WT1 (Wilms' tumor gene) antisense oligodeoxynucleotides: implications for the involvement of WT1 in leukemogenesis," Blood 87(7):2878-2884, 1996.
International Preliminary Report on Patentability for App. Ser. No. PCT/JP2005/005824, dated Feb. 14, 2005, 8 pages.
International Search Report App. Ser. No. PCT/JP2005/005824, mailed Jul. 5, 2005, 4 pages.
USPTO Restriction Requirement in U.S. Appl. No. 10/594,939, mailed Oct. 16, 2008, 10 pages.
Fish & Richardson P.C., Response to Restriction Requirement dated Oct. 16, 2008 in U.S. Appl. No. 10/594,939, filed Nov. 14, 2008, 1 page.
USPTO Non-Final Office Action in U.S. Appl. No. 10/594,939, mailed Jan. 22, 2009, 27 pages.
Fish & Richardson P.C., Amendment in Reply to Action dated Jan. 22, 2009 in U.S. Appl. No. 10/594,939, filed Jul. 21, 2009, 14 pages.
Restriction Requirement in U.S. Appl. No. 10/594,939, mailed Feb. 18, 2010, 8 pages.
Fish & Richardson P.C., Response to Restriction Requirement dated Feb. 18, 2010 in U.S. Appl. No. 10/594,939, filed Aug. 12, 2010, 1 page.
Final Office Action in U.S. Appl. No. 10/594,939, mailed Oct. 26, 2010, 17 pages.
Fish & Richardson P.C., Amendment in Reply to Action dated Oct. 26, 2010 in U.S. Appl. No. 10/594,939, filed Nov. 21, 2011, 12 pages.
Non-Final Office Action in U.S. Appl. No. 10/594,939, mailed Dec. 22, 2011, 16 pages.
Fish & Richardson P.C., Amendment in Reply to Action dated Dec. 22, 2011 in U.S. Appl. No. 10/594,939, filed Apr. 20, 2012, 11 pages.
Fish & Richardson P.C., Supplemental Amendment in U.S. Appl. No. 10/594,939, filed Jun. 26, 2012, 7 pages.
Notice of Allowance in U.S. Appl. No. 10/594,939, mailed Jul. 3, 2012, 5 pages.
International Preliminary Report on Patentability for App. Ser. No. PCT/JP2005/005790, 6 pages.
International Search Report App. Ser. No. PCT/JP2005/005790, mailed Jun. 7, 2005, 2 pages.
USPTO Restriction Requirement in U.S. Appl. No. 10/594,706, mailed Mar. 31, 2009, 5 pages.
Fish & Richardson P.C., Response to Restriction Requirement dated Mar. 31, 2009 in U.S. Appl. No. 10/594,706, filed Apr. 29, 2009, 1 page.
USPTO Non-Final Office Action in U.S. Appl. No. 10/594,706, mailed Jun. 3, 2009, 23 pages.
Fish & Richardson P.C., Amendment in Reply to Action dated Jun. 3, 2009 in U.S. Appl. No. 10/594,706, filed Dec. 2, 2009, 16 pages.
USPTO Final Office Action in U.S. Appl. No. 10/594,706, mailed Mar. 10, 2010, 13 pages.
Fish & Richardson P.C., Amendment in Reply to Final Office Action dated Mar. 10, 2010 in U.S. Appl. No. 10/594,706, filed Sep. 9, 2010, 8 pages.
USPTO Final Office Action in U.S. Appl. No. 10/594,706, mailed Feb. 7, 2011, 18 pages.
Fish & Richardson P.C., Reply to Final Office Action dated Feb. 7, 2011 in U.S. Appl. No. 10/594,706, filed Aug. 4, 2011, 9 pages.
Homo sapiens Wilms tumor 1 (WT1), mRNA, GenBank Accession No. NM_000378, Nov. 5, 2000, accessed at http://www.ncbi.nlm.nih.gov/nuccore/NM_000378.1 on Jul. 10, 2013, 2 pages.
USPTO Non-Final Office Action in U.S. Appl. No. 10/594,706, mailed Jul. 16, 2013, 10 pages.

FIG. 2

|            | WRI-4 | MOCK |
|-----------:|:-----:|:----:|
| 17AA(+) —  |       |      |
| 17AA(−) —  |       |      |

SIRNA THAT INHIBITS WT1 GENE EXPRESSION AND USES THEREOF

CROSS-REFERENCE TO RELATED APPLICATIONS

This application is a continuation of U.S. application Ser. No. 10/594,939, filed Aug. 2, 2007 (now U.S. Pat. No. 8,299, 234), which is the National Stage of International Application No. PCT/JP2005/005824, filed on Mar. 29, 2005, which claims the benefit of Japanese Patent Application Serial No. 2004-096876, filed on Mar. 29, 2004. The contents of all of the foregoing applications are hereby incorporated by reference in their entireties.

BACKGROUND ART

Wilms tumor gene (WT1 gene) is a zinc-finger transcription factor-encoding gene. WT1 gene is known to have four isoforms distinguished by the presence or absence of 17 amino acids (17AA) inserted at the 5'-side site of the two alternative splicing sites of the gene, as well as by the presence or absence of three amino acid residues between zinc fingers 3 and 4.

Wilms tumor gene (WT1 gene) was isolated as a causative gene of pediatric kidney tumor (Non-patent Documents 1 and 2). Since some deletions and mutations in this gene have been found in Wilms tumor, it has been believed that this gene is a tumor suppressor gene.

However, a number of reports by the present inventors suggest that WT1 gene exerts an oncogene-like function rather than functions as a tumor suppressor gene. It has been revealed that almost all leukemia cells express high levels of the nonmutated wild type WT1 gene, and the expression level in leukemia is reciprocally correlated with the prognosis of patients (Non-patent Documents 3 and 4); antisense WT1 DNA specifically suppresses the growth of leukemia cells (Non-patent Document 5); forced expression of the WT1 gene results in suppression of the differentiation of mouse normal bone marrow precursor cells and bone marrow precursor cell line 32D C13 into neutrophils, and the cells began proliferating as a result (Non-patent Document 6); etc. These findings suggest that the WT1 gene is involved in the leukemogenic conversion of hematopoietic cells. The present inventors have also reported that the wild type WT1 gene is expressed at high levels in various types of solid cancers (Non-patent Documents 7 to 14).

The present inventors believe that the WT1 gene would be useful for the development of tumor-specific molecular target therapy if expression of the gene can be efficiently suppressed. To date, no tumor-specific molecular target therapy that targets WT1 has been known.

[Non-patent Document 1] Call K M, et al.: Isolation and characterization of a zinc finger polypeptide gene at the human chromosome 11 Wilms' tumor locus. Cell 60: 509, 1990

[Non-patent Document 2] Gessler M, et al.: Homozygous deletion in Wilms tumours of a zinc-finger gene identified by chromosome jumping. Nature 343'. 774, 1990

[Non-patent Document 3] Inoue K, et al.: WT1 as a new prognostic factor and a new marker for the detection of minimal residual disease in acute leukemia. Blood 84: 3071, 1994

[Non-patent Document 4] Inoue K, et al.: Aberrant overexpression of the Wilms tumor gene (WT1) in human leukemia. Blood 89: 1405, 1997

[Non-patent Document 5] Yamagami T, Sugiyama H, Inoue K, Ogawa H, Tatekawa T, Hirata M, Kudoh T, Akiyama T, Murakami A, Maekawa T. Growth inhibition of human leukemic cells by WT1 (Wilms tumor gene) antisense oligodeoxynucleotides: implications for the involvement of WT1 in leukemogenesis. Blood. 1996 Apr. 1; 87(7):2878-84.

[Non-patent Document 6] Inoue K, et al.: Wilms' tumor gene (WT1) competes with differentiation-inducing signal in hematopoietic progenitor cells. Blood 91:2969,1998

[Non-patent Document 7] Oji, Y., Ogawa, H., Tamaki, H., Oka, Y., Tsuboi, A., Kim, E. H., Soma, T., Tatekawa, T., Kawakami, M., Asada, M., Kishimoto, T., and Sugiyama, H. Expression of the Wilms' tumor gene WT1 in solid tumors and its involvement in tumor cell growth. Japanese Journal of Cancer Research, 90: 194-204, 1999.

[Non-patent Document 8] Oji, Y., Miyoshi, S., Maeda, H., Hayashi, S., Tamaki, H., Nakatsuka, S., Yao, M., Takahashi, E., Nakano, Y., Hirabayashi, H., Shintani, Y., Oka, Y., Tsuboi, A., Hosen, N., Asada, M., Fujioka, T., Murakami, M., Kanato, K., Motomura, M., Kim, E. H., Kawakami, M., Ikegame, K., Ogawa, H., Aozasa, K., Kawase, I., and Sugiyama, H. Overexpression of the Wilms' tumor gene WT1 in de novo lung cancers. International Journal of Cancer, 100(3): 297-303, 2002.

[Non-patent Document 9] Ueda, T., Oji, Y., Naka, N., Nakano, Y., Takahashi, E., Koga, S., Asada, M., Ikeba, A., Nakatsuka, S., Abeno, S., Hosen, N., Tomita, Y., Aozasa, K., Tamai, N., Myoui, A., Yoshikawa, H., and Sugiyama, H. Overexpression of the Wilms' tumor gene WT1 in human bone and soft-tissue sarcomas. Cancer Science, 94: 271-276, 2003.

[Non-patent Document 10] Oji, Y., Inohara, H., Nakazawa, M., Nakano, Y., Akahani, S., Nakatusuka, S., Koga, S., Abeno, S., Honjo, Y, Yamamoto, Y., Iwai, S., Yoshida, K., Oka, Y., Ogawa, H., Yoshida, J., Aozasa, K., Kubo, T., and Sugiyama, H. Overexpression of the Wilms' tumor gene WT1 in head and neck squamous cell carcinoma. Cancer Science, 94: 523-529, 2003.

[Non-patent Document 11] Oji, Y., Miyoshi, Y., Koga, S., Nakano, Y., Ando, A., Nakatuska, S., Ikeba, A., Takahashi, E., Sakaguchi, N., Yokota, A., Hosen, N., Ikegame, K., Kawakami, M., Tsuboi, A., Oka, Y., Ogawa, H., Aozasa, K., Noguchi, S., and Sugiyama, H. Overexpression of the Wilms' tumor gene WT1 in primary thyroid cancer. Cancer Science, 94: 606-611, 2003.

[Non-patent Document 12] Oji, Y., Yamamoto, H., Nomura, M., Nakano, Y., Ikeba, A., Nakatsuka, S., Abeno, S., Kiyotoh, E., Jomgeow, T., Sekimoto, M., Nezu, R., Yoshikawa, Y., Inoue, Y., Hosen, N., Kawakami, M., Tsuboi, A., Oka, Y., Ogawa, H., Souda, S., Aozasa, K., Monden, M., and Sugiyama, H. Overexpression of the Wilms' tumor gene WT1 in colorectal adenocarcinoma. Cancer Science, 94: 712-717, 2003.

[Non-patent Document 13] Oji, Y., Miyoshi, S., Takahashi, E., Koga, S., Nakano, Y., Shintani, Y., Hirabayashi, H., Matsumura, A., Iuchi, K., Ito, K., Kishimoto, Y., Tsuboi, A., Ikegame, K., Hosen, N., Oka, Y., Ogawa, H., Maeda, H., Hayashi, S., Kawase, I., and Sugiyama, H. Absence of mutations in the Wilms' tumor gene WT1 in de novo non-small cell lung cancers. Neoplasma, 51:17-20, 2004.

[Non-patent Document 14] Oji, Y., Miyoshi, Y., Kiyotoh, E., Koga, S., Nakano, Y., Ando, A., Hosen, N., Tsuboi, A., Kawakami, M., Ikegame, K., Oka, Y., Ogawa, H., Noguchi, S., and Sugiyama, H. Absence of mutations in the Wilms' tumor gene WT1 in primary breast cancer. Jpn J Clin Oncol, 34:74-7, 2004.

[Non-patent Document 15] Oji Y, Suzuki T, Nakano Y, Maruno M, Nakatsuka S, Jomgeow T, Abeno S, Tatsumi N, Yokota A, Aoyagi S, Nakazawa T, Ito K, Kanato K, Shirakata T, Nishida S, Hosen N, Kawakami M, Tsuboi A, Oka Y, Aozasa K, Yoshimine T, Sugiyama H, Overexpression of the Wilms' tumor gene WT1 in primary astrocytic tumors. Cancer Sci. 95:822-7, 2004.

[Non-patent Document 16] Oji Y, Yano M, Nakano Y, Abeno S, Nakatsuka S, Ikeba A, Yasuda T, Fujiwara Y, Takiguchi S, Yamamoto H, Fujita S, Kanato K, Ito K, Jomgeow T, Kawakami M, Tsuboi A, Shirakata T, Nishida S, Hosen N, Oka Y, Aozasa K, Monden M, Sugiyama H., Overexpression of the Wilms' tumor gene WT1 in esophageal cancer. Anticancer Res. 24:3103-8, 2004.

[Non-patent Document 17] Oji Y, Nakamori S, Fujikawa M, Nakatsuka S, Yokota A, Tatsumi N, Abeno S, Ikeba A, Takashima S, Tsujie M, Yamamoto H, Sakon M, Nezu R, Kawano K, Nishida S, Ikegame K, Kawakami M, Tsuboi A, Oka Y, Yoshikawa K, Aozasa K, Monden M, Sugiyama H. Overexpression of the Wilms' tumor gene WT1 in pancreatic ductal adenocarcinoma. Cancer Sci. 95:583-7, 2004.

DISCLOSURE OF THE INVENTION

An objective of the present invention is to provide molecules that can efficiently suppress WT1 gene expression, and also to provide cell growth-suppressing agents and cell death-inducing agents comprising such a molecule as an active ingredient. In particular, the present invention provides siRNAs, DNAs encoding such siRNAs, and vectors comprising such DNAs, as WT1 gene expression-suppressing molecules.

To accomplish the above-mentioned objective, the present inventors considered suppressing WT1 expression using a vector that allows siRNA, which has attracted attention in recent years as a means for suppressing gene expression, to be expressed in cancer cells. As a result of trial and error, the present inventors discovered that siRNAs, which comprise an RNA complementary to the WT1 gene transcript and a complementary strand of the RNA, not only suppress WT1 gene expression but also demonstrate a remarkable cell growth-suppressing effect on cancer cell lines. In addition, the present inventors discovered that these siRNAs have effects of inducing mitochondria-mediated cell death and enhancing sensitivity of cancer cells to anticancer agents or cell death-inducing agents.

That is, the present inventors succeeded in developing cell growth-suppressing agents and cell death-inducing agents that utilize WT1-targeting RNAi effects, and therefore completed the present invention.

More specifically, the present invention provides:

[1] a cell growth-suppressing agent comprising any one of (a) to (c) as an active ingredient:
  (a) a double-stranded RNA comprising an RNA complementary to a WT1 gene transcript, and an RNA complementary to said RNA;
  (b) a DNA encoding the double-stranded RNA of (a); and
  (c) a vector into which the DNA of (b) has been inserted;

[2] the cell growth-suppressing agent of [1], wherein the double-stranded RNA comprises an RNA complementary to a 17AA site of a WT1 gene transcript, and an RNA complementary to said RNA;

[3] the cell growth-suppressing agent of [1], wherein the double-stranded RNA comprises an RNA complementary to the nucleotide sequence of SEQ ID NO: 1 present in a 17AA site of a WT1 gene transcript, and an RNA complementary to said RNA;

[4] the cell growth-suppressing agent of [1], wherein the double-stranded RNA comprises the pair of the nucleotide sequence of SEQ ID NO: 1 and the nucleotide sequence of SEQ ID NO: 2;

[5] the cell growth-suppressing agent of [1], wherein the double-stranded RNA comprises an RNA encoded by the DNA of any one of (a) to (c), and an RNA complementary to said RNA:
  (a) a DNA comprising the nucleotide sequence of any one of SEQ ID NOs: 9, 12, 14, and 16;
  (b) a DNA that hybridizes under stringent conditions with a DNA comprising the nucleotide sequence of any one of SEQ ID NOs: 9, 12, 14, and 16; and
  (c) a DNA comprising the nucleotide sequence of any one of SEQ ID NOs: 11, 13, 15, and 17.

[6] the cell growth-suppressing agent of any one of [1] to [5], wherein the agent targets a cancer cell;

[7] the cell growth suppressing agent of any one of [1] to [5], wherein the agent targets any one of a fibrosarcoma cell, colon cancer cell, leukemia cell, and gastric cancer cell;

[8] a cell death-inducing agent comprising any one of (a) to (c) as an active ingredient:
  (a) a double-stranded RNA comprising an RNA complementary to a WT1 gene transcript, and an RNA complementary to said RNA;
  (b) a DNA encoding the double-stranded RNA of (a); and
  (c) a vector into which the DNA of (b) has been inserted;

[9] the cell death-inducing agent of [8], wherein the double-stranded RNA comprises an RNA encoded by the DNA of any one of (a) to (c), and an RNA complementary to said RNA:
  (a) a DNA comprising the nucleotide sequence of any one of SEQ ID NOs: 9, 12, 14, and 16;
  (b) a DNA that hybridizes under stringent conditions with a DNA comprising the nucleotide sequence of any one of SEQ ID NOs: 9, 12, 14, and 16; and
  (c) a DNA comprising the nucleotide sequence of any one of SEQ ID NOs: 11, 13, 15, and 17;

[10] the cell death-inducing agent of [8] or [9], wherein the agent induces cell death through mitochondria;

[11] the cell death-inducing agent of any one of [8] to [10], wherein the agent targets a cancer cell;

[12] the cell death-inducing agent of any one of [8] to [10], wherein the agent targets any one of a fibrosarcoma cell, colon cancer cell, leukemia cell, and gastric cancer cell;

[13] an agent that enhances cancer cell sensitivity to an anti-cancer agent, wherein the agent comprises any one of (a) to (c) as an active ingredient:
  (a) a double-stranded RNA comprising an RNA complementary to a WT1 gene transcript, and an RNA complementary to said RNA;
  (b) a DNA encoding the double-stranded RNA of (a); and
  (c) a vector into which the DNA of (b) has been inserted;

[14] the agent of [13], wherein the double-stranded RNA comprises an RNA encoded by the DNA of any one of (a) to (c), and an RNA complementary to said RNA:
  (a) a DNA comprising the nucleotide sequence of any one of SEQ ID NOs: 9, 12, 14, and 16;
  (b) a DNA that hybridizes under stringent conditions with a DNA comprising the nucleotide sequence of any one of SEQ ID NOs: 9, 12, 14, and 16; and
  (c) a DNA comprising the nucleotide sequence of any one of SEQ ID NOs: 11, 13, 15, and 17;

[15] an agent that enhances cancer cell sensitivity to a cell death-inducing agent, wherein the agent comprises any one of (a) to (c) as an active ingredient:

(a) a double-stranded RNA comprising an RNA complementary to a WT1 gene transcript, and an RNA complementary to said RNA;
(b) a DNA encoding the double-stranded RNA of (a); and
(c) a vector into which the DNA of (b) has been inserted;

[16] the agent of [15], wherein the double-stranded RNA comprises an RNA encoded by the DNA of any one of (a) to (c), and an RNA complementary to said RNA:
(a) a DNA comprising the nucleotide sequence of any one of SEQ ID NOs: 9, 12, 14, and 16;
(b) a DNA that hybridizes under stringent conditions with a DNA comprising the nucleotide sequence of any one of SEQ ID NOs: 9, 12, 14, and 16; and
(c) a DNA comprising the nucleotide sequence of any one of SEQ ID NOs: 11, 13, 15, and 17;

[17] an agent that eliminates mitochondrial membrane potential in a cancer cell, wherein the agent comprises any one of (a) to (c) as an active ingredient:
(a) a double-stranded RNA comprising an RNA complementary to a WT1 gene transcript, and an RNA complementary to said RNA;
(b) a DNA encoding the double-stranded RNA of (a); and
(c) a vector into which the DNA of (b) has been inserted;

[18] the agent of [17], wherein the double-stranded RNA comprises an RNA encoded by the DNA of any one of (a) to (c), and an RNA complementary to said RNA:
(a) a DNA comprising the nucleotide sequence of any one of SEQ ID NOs: 9, 12, 14, and 16;
(b) a DNA that hybridizes under stringent conditions with a DNA comprising the nucleotide sequence of any one of SEQ ID NOs: 9, 12, 14, and 16; and
(c) a DNA comprising the nucleotide sequence of any one of SEQ ID NOs: 11, 13, 15, and 17;

[19] an agent that enhances cytochrome c release into cytoplasm, wherein the agent comprises any one of (a) to (c) as an active ingredient:
(a) a double-stranded RNA comprising an RNA complementary to a WT1 gene transcript, and an RNA complementary to said RNA;
(b) a DNA encoding the double-stranded RNA of (a); and
(c) a vector into which the DNA of (b) has been inserted; and

[20] the agent of [19], wherein the double-stranded RNA comprises an RNA encoded by the DNA of any one of (a) to (c), and an RNA complementary to said RNA:
(a) a DNA comprising the nucleotide sequence of any one of SEQ ID NOs: 9, 12, 14, and 16;
(b) a DNA that hybridizes under stringent conditions with a DNA comprising the nucleotide sequence of any one of SEQ ID NOs: 9, 12, 14, and 16; and
(c) a DNA comprising the nucleotide sequence of any one of SEQ ID NOs: 11, 13, 15, and 17.

BRIEF DESCRIPTION OF THE DRAWINGS

FIG. 2 is a photograph that shows suppression of 17AA(+) WT1 mRNA expression by a vector-based WT1 siRNA.

Figure 1:
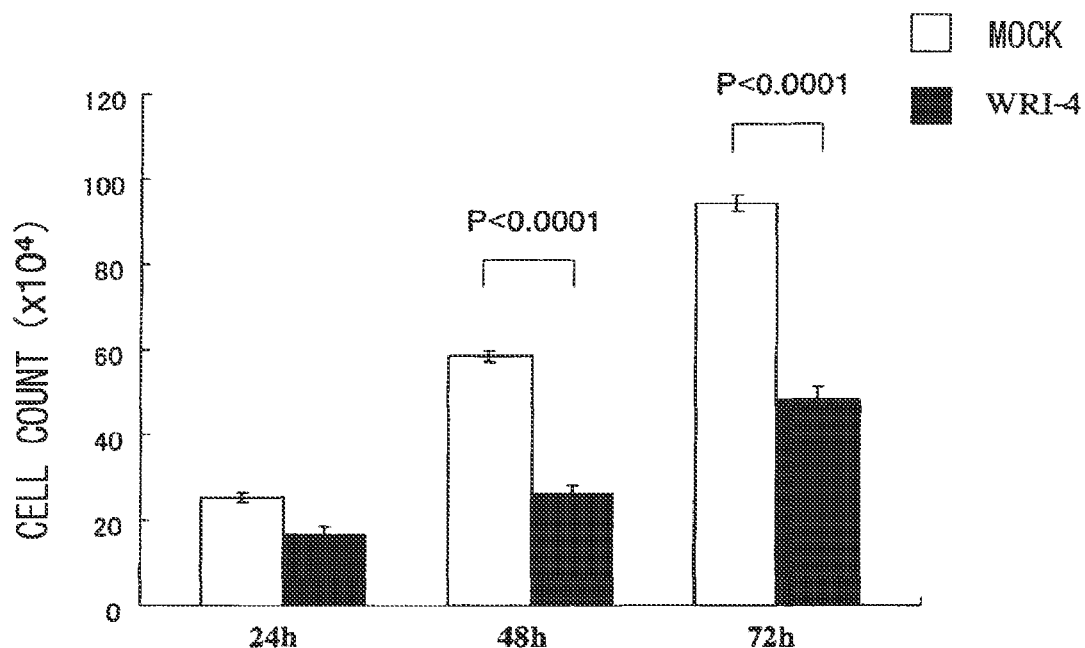
FIG. 1 shows suppression of HT-1080 cell growth by a vector-based WT1 siRNA.

DETAILED DESCRIPTION siRNAs of the present invention are double-stranded RNAs in which an RNA complementary to a transcript of the target WT1 gene (antisense RNA strand) is paired with an RNA complementary to this RNA (sense RNA strand). The sequence of the WT1 gene transcript that becomes the target of siRNAs of the present invention is not particularly limited so long as the siRNAs can show RNAi effects. Preferably, the sequence exists in the 17AA site of the WT1 gene transcript. As used herein, "17AA site" refers to a site corresponding to 17 amino acids of the WT1 gene transcript sequence in the 5' side site of the two alternative splicing sites present in the WT1 gene. A specific example of such a target sequence includes the sequence of SEQ ID NO: 1. The nucleotide sequences of the sense strand and antisense strand of an siRNA directed against the 17AA site of the WT1 gene transcript used in the Examples are shown in SEQ ID NOs: 1 and 2, respectively. siRNAs of the present invention comprising the nucleotide sequence of SEQ ID NO: 1 paired with the nucleotide sequence of SEQ ID NO: 2 are particularly preferred.

siRNA refers to a short double-stranded RNA chain whose length is in a range that does not show toxicity in cells. Its length is not particularly limited, so long as the length is within a range that does not show toxicity. For example, the length may be 15 to 49 base pairs, and preferably 15 to 30 base pairs.

The portion of the double-stranded RNA where RNAs are paired is not limited to the part that is completely paired, and it may include unpaired portions caused by mismatches (wherein the corresponding nucleotides are not complementary), bulges (wherein one of the strands lacks corresponding nucleotides), and such.

The terminal structure of an siRNA of the present invention may be a blunt end or a sticky (overhanging) end, so long as the structure can suppress WT1 gene expression by RNAi effects. The sticky (overhanging) end structure is not limited to only a structure protruding from the 3' terminal side, and also includes a structure protruding from the 5' terminal side, so long as it is capable of inducing RNAi effects. The number of overhanging nucleotides is not limited to 2 or 3 nucleotides as reported, and can be any number of nucleotides that can induce RNAi effects. For example, the number of nucleotides may be 1 to 8 nucleotides, and preferably 2 to 4 nucleotides. Since this overhanging sequence has low specificity to the WT1 gene transcript, it is not necessary for the sequence to be complementary (antisense) or identical (sense) to the target WT1 gene transcript sequence.

siRNAs of the present invention can be prepared by selecting a target sequence based on the WT1 gene, or preferably a nucleotide sequence of the 17AA(+) isoform. The 17AA(+) isoform refers to an isoform comprising the above-described 17AA. The present inventors have shown that among the four isoforms of WT1, 17AA(+) plays an oncogene-like function (Non-patent Documents 6 and 7). For example, siRNA preparation is carried out by selecting as a target sequence, a continuous region of a transcript mRNA based on the WT1 gene nucleotide sequence, or preferably by selecting the 17AA site region. Double-stranded RNA corresponding to the selected region can be suitably prepared by methods such as in vitro chemical synthesis, in vitro transcription using phage RNA polymerase, and performing RNaseIII or Dicer digestion on a long dsRNA transcribed and assembled based on a cloned cDNA. The cDNA sequence of the human WT1 gene used in the Examples is shown in SEQ ID NO: 6. The 17AA site of the WT1 gene corresponds to positions 1137 to 1187 in the sequence of SEQ ID NO: 6. The WT1 gene is registered in NCBI GENBANK as NM_024426.

The siRNAs of the present invention can be prepared by selecting a target sequence based on the nucleotide sequence of an arbitrary site in the WT1 gene.

Examples of a preferred nucleotide sequence in the WT1 gene include positions 1150-1179 (SEQ ID NO: 9), positions 1710-1739 (SEQ ID NO: 12), positions 2578-2607 (SEQ ID NO: 14), and positions 2906-2935 (SEQ ID NO: 16) in SEQ ID NO: 6 and nucleotide sequences of DNAs that hybridize under stringent conditions to these sequences. As used herein, the phrase "hybridize under stringent conditions" refers to a situation, where under appropriate stringency hybridization conditions, a nucleic acid molecule with a predetermined sequence (that is, a second polynucleotide), when present in a DNA or RNA sample, hybridizes to form a double strand, or inherently binds only to each other. For example, stringent conditions are ordinarily 42° C., 2× SSC, and 0.1% SDS, preferably 50° C., 2× SSC, and 0.1% SDS, and more preferably 65° C., 0.1× SSC, and 0.1% SDS, but are not particularly limited to these conditions. Factors that affect hybridization stringency are considered to be temperature, salt concentration, and a number of other factors, and those skilled in the art can appropriately select these factors to achieve the optimal stringency.

Examples of a DNA that hybridizes under stringent conditions include more preferably DNAs comprising the nucleotide sequence of any one of SEQ ID NOs: 11, 13, 15, and 17.

siRNAs of the present invention can be expressed in cells using a DNA encoding an above-mentioned antisense RNA strand (hereinafter referred to as antisense coding DNA), and a DNA encoding an above-mentioned sense RNA strand (hereinafter referred to as sense coding DNA) (hereinafter, antisense coding DNA and sense coding DNA will be collectively referred to as DNAs of the present invention). The "antisense coding DNA" and "sense coding DNA" can be introduced into the chromosome of a cell with a promoter as they are to intracellularly express antisense RNA and sense RNA, and thereby form siRNA; however, preferably, a vector is made to carry the siRNA expression system so that cells can be transfected efficiently. The "vector" that can be used herein can be selected according to the cell to be transfected and such. For mammalian cells, examples include viral vectors such as retrovirus vector, adenovirus vector, adeno-associated virus vector, vaccinia virus vector, lentivirus vector, herpesvirus vector, alphavirus vector, EB virus vector, papilloma virus vector, and foamyvirus vector, and non-viral vectors including cationic liposome, ligand DNA complex, and gene gun (Y. Niitsu, et al., Molecular Medicine 35: 1385-1395 (1998)), but are not limited thereto. It is also preferable to use, instead of virus vectors, dumbbell-shaped DNA (Zanta M. A. et al., Gene delivery: a single nuclear localization signal peptide is sufficient to carry DNA to the cell nucleus. Proc Natl Acad Sci USA. 1999 Jan. 5; 96 (1): 91-6), DNA modified to have nuclease resistance, or naked plasmids (Liu F, Huang L. Improving plasmid DNA-mediated liver gene transfer by prolonging its retention in the hepatic vasculature. J. Gene Med. 2001 November-December; 3(6): 569-76).

The construct for maintaining a DNA encoding an siRNA of the present invention in a vector, may express the antisense RNA strand and sense RNA strand from a same vector or express the respective antisense RNA strand and sense RNA from different vectors. For example, the construct for expressing both antisense RNA and sense RNA from a same vector can be prepared by linking a promoter, such as the pol III system, which is capable of expressing short RNA, to the upstream of an antisense coding DNA and a sense coding DNA, respectively, to form an antisense RNA expression cassette and a sense RNA expression cassette, and inserting these cassettes into a vector either in the same direction or in opposite directions. It is also possible to construct an expression system in which antisense coding DNA and sense coding DNA are placed on different strands in opposite orientations so as to form a pair. This construct is equipped with one double-stranded DNA (siRNA coding DNA) comprising paired antisense RNA coding strand and sense RNA coding strand, and this double-stranded DNA is equipped on both sides with a promoter opposite to each other so as to express antisense RNA and sense RNA from the respective DNA strands. In this case, to avoid addition of excess sequences downstream of the sense RNA and antisense RNA, it is preferable to place a terminator at the 3' end of the respective strands (antisense RNA coding strand and sense RNA coding strand). A continuous sequence of four or more adenine (A) nucleotides may be used as the terminator. In this palindrome expression system, it is preferable to use two different promoters.

A construct that forms a double-stranded RNA comprising a hairpin structure (self-complementary 'hairpin' RNA (hpRNA)) (Smith, N. A. et al. Nature, 407:319, 2000; Wesley, S. V. et al. Plant J. 27:581, 2001; Piccin, A. et al. Nucleic Acids Res. 29:E55, 2001), in which an appropriate sequence (preferably an intron sequence) is inserted between inverted repeats of a target sequence, can be used as a DNA to be inserted into a vector encodes the siRNA of the present invention.

In the present invention, the nucleotide sequence inserted between inverted repeats of a target sequence is not particularly limited, but is preferably, for example, the nucleotide sequence (loop 1) of SEQ ID NO: 18 or the loop sequence AAAACTCGAGAAAA of SEQ ID NO: 3, and more preferably the nucleotide sequence (loop 2) of SEQ ID NO: 19.

A construction for expressing antisense RNA and sense RNA from different vectors may be achieved, for example, by linking a pol III promoter capable of expressing short RNAs to the upstream of antisense coding DNA and the upstream of sense coding DNA, respectively, to construct an antisense RNA expression cassette and a sense RNA expression cassette, and introducing these cassettes into different vectors.

The "siRNA (double-stranded RNA)-encoding DNA" of the present invention may be a single DNA encoding both strands of an siRNA, or a pair of DNAs encoding each of the strands. The "vector into which the siRNA (double-stranded RNA)-encoding DNA has been inserted" may be a single vector expressing the respective strands of siRNA as two transcripts, a single vector expressing both of the siRNA strands as a single transcript, or two vectors expressing the respective siRNA strands.

It is not necessary for the DNA used in RNAi to be completely identical to the target gene, and it has a sequence identity of at least 70% or more, preferably 80% or more, more preferably 90% or more, and most preferably 95% or more (for example, 96%, 97%, 98%, 99% or more) with the target gene. The sequence identity of nucleotide sequences can be determined using Karlin and Altschul's BLAST algorithm (Proc. Natl. Acad. Sci. USA 90:5873-5877, 1993). A program called BLASTN has been developed based on this algorithm (Altschul et al. J. Mol. Biol. 215: 403-410 (1990)). When nucleotide sequences are analyzed using BLASTN based on BLAST, parameters are set, for example, at score=100 and wordlength=12. When using the BLAST and Gapped BLAST programs, the default parameters for the respective programs are used. Specific techniques for these analytical methods are well known.

siRNAs of the present invention, DNAs encoding these siRNAs, and vectors inserted with such DNAs can be individually used as an agent of the present invention as they are, or by mixing with an appropriate compounding agent. By introducing an agent of the present invention into cells using known transfection agents and such, RNAi effects will be exerted in the cells, and effects of the agent of the present invention will be realized.

Examples of the "effects of the agent" of the present invention include cell growth-suppressing effects, cell death-inducing effects, and effects of enhancing the sensitivity of cancer cells to anticancer agents or cell death-inducing agents. Further examples of the effects of the present invention include effects of eliminating mitochondrial membrane potential, and effects of enhancing the cytochrome c release from mitochondria to cytoplasm in cancer cells.

The effects may be temporary effects, or effects that are eventually expressed after a certain amount of time has passed.

Examples of the effects of inducing cell death (apoptosis) in the present invention preferably include effects of inducing the mitochondria-mediated cell death, but are not limited thereto.

When addition of an agent of the present invention to cancer cells is confirmed to eliminate mitochondrial membrane potential and enhance cytochrome c release into the cytoplasm in cancer cells, cell death is considered to be induced.

In the present invention, the anticancer agents which cancer cells have enhanced sensitivity for are not particularly limited, but preferred examples include doxorubicin and etoposide. The cell death-inducing agents of the present invention which cancer cells have enhanced sensitivity for are not particularly limited, but a preferred example is a cancer cell-specific cell death-inducing agent, TRAIL.

Cells in which effects of the agents of the present invention are expected are cells that express the WT1 gene. An example of such cells is cancer cells. More specifically, examples of such cells include cancer cells of leukemia, colon cancer, lung cancer, breast cancer, head and neck squamous cell carcinoma, esophageal cancer, gastric cancer, thyroid cancer, bone and soft tissue sarcoma, ovarian cancer, uterine cancer, kidney cancer, pancreatic cancer, and glioblastoma. Cancer cells of the present invention are not particularly limited in the present invention, but examples preferably include fibrosarcoma cells, colon cancer cells, leukemia cells, and gastric cancer cells, and more preferably include HT-1080, HL-60, SW620, and AZ-521. Therefore, agents of the present invention may be effective not only for academic research, but also as pharmaceuticals for cancer treatment, and especially as pharmaceuticals for cancer treatment targeting the cancers listed above.

When using an agent of the present invention as a pharmaceutical for treating cancer, such an agent can be formulated appropriately. In such formulation, pharmaceutically acceptable compounding ingredients may be mixed. Examples of pharmaceutically acceptable compounding agents include surfactants, excipients, colors, flavors, preservatives, stabilizers, buffers, suspending agents, tonicity adjusting agents, binding agents, disintegrators, lubricants, fluidity enhancers, and corrigents, but are not limited thereto and other conventional carriers may be used appropriately. The types of dosage forms of the above-mentioned formulation include tablets, epipastics, pills, powders, granules, fine granules, soft/hard capsules, film-coated preparations, pellets, sublingual preparations, and paste as oral preparations, and include injections, suppositories, transdermal preparations, ointments, plasters, and liquids for external use as parenteral preparations, and those skilled in the art can select the most appropriate dosage form depending on the administration route, administration target, and such. For in vivo administration of a DNA of the present invention, virus vectors such as retroviruses, adenoviruses, or Sendai viruses, or non-viral vectors such as liposomes may be used. Examples of the method of administration include in vivo and ex vivo methods.

All prior art references cited herein are incorporated by reference into this description.

EXAMPLES

The present invention is described in detail below with reference to Examples, but it is not to be construed as being limited thereto.

<Cells Used in the Examples>

In the following Examples, four WT1-expressing cell lines: HT-1080 fibrosarcoma cells, AZ-521 gastric cancer cells, SW620 colon cancer cells, and HL-60 promyelocytic leukemia cells; and one non-WT1-expressing cell line: PC-14 lung cancer cells were used. HT-1080, AZ-521, and PC-14 were cultured at 37° C. under 5% $CO_2$ in 10% FBS-containing DMEM, and SW620 and HL-60 were cultured in 10% FBS-containing RPMI.

Example 1

Production of siRNA expression vector that targets the WT1 Gene mRNA 17AA site

The DNA to be inserted for generating an siRNA expression vector that targets the WT1 gene mRNA 17 AA site was produced. The specific location of the targeted site was positions 1150 to 1179 of the WT1 gene sequence shown in SEQ ID NO: 6. The sequence that was produced is shown below (SEQ ID NO: 3): 5'-C CCT TCT GTC CAT TTC ACT GAG CTG GAG CT (DNA encoding a 30-mer antisense strand of the target RNA)- (SEQ ID NO:20) -AAAACTCGAGAAAA (loop sequence containing an XhoI site)- (SEQ ID NO:21) -AG CTC CAG CTC AGT GAA ATG GAC AGA AGG G (DNA encoding a 30-mer sense strand of the target RNA)- (SEQ ID NO:22) -GGTACCCCGGATATCTTTTTTT-3' - (SEQ ID NO:23).

The DNA was inserted into the cloning site of an siRNA expression vector to produce WRI-4 vector. An siRNA expression vector (pPuro-tRNA-SKE vector), gift from Dr. H. Kawasaki at the Graduate School of Engineering at the University of Tokyo, was used as the siRNA expression vector. The piGENEtRNA Pur Vector (Clontech) may also be used instead of the pPuro-tRNA-SKE vector.

WRI-3 vector was produced as an siRNA expression vector targeting a sequence common to the four isoforms of WT1 gene mRNA. The WRI-3 vector comprises aag gtg gct cct aag ttc atc tga ttc cag (an antisense RNA strand-encoding DNA; SEQ ID NO: 4), and ctg gaa tca gat gaa ctt agg agc cac ctt (a sense RNA strand-encoding DNA; SEQ ID NO: 5). The site targeted by WRI-3 is positions 1101 to 1130 of the WT1 gene sequence shown in SEQ ID NO: 6.

Example 2

Cell Culturing and Introduction of siRNA Expression Vector

Fibrosarcoma cell line HT-1080 cells that express high levels of the WT1 gene were cultured in Dulbecco's Modified Medium (DMEM) containing 10% FBS. Trypsinized HT-1080 cells were plated onto a 6-well plate at $2 \times 10^4$ cells/2 ml, and 24 hours later, 2 μg of the WRI-4 vector or an empty vector was introduced into HT-1080 cells using Fugene 6 (ROCHE).

Example 3

Growth Suppression of HT-1080 Cells by siRNA Expression Vector

Cell growth-suppressing effect of the WRI-4 vector was examined. HT-1080 cells transfected with the vector were cultured for 24, 48, or 72 hours, and the number of cells was counted. After trypsinization, the number of cells was calculated using a cytometer.

When an siRNA expression vector directed against WT1 was introduced into HT-1080 cells, growth of the HT-1080 cells was significantly suppressed compared to when an empty control vector was introduced. The results are shown in FIG. 1.

When the WRI-3 expression vector was introduced into HT-1080 cells, and cell growth-suppressing effects were examined, a certain level of cell growth-suppressing effect could be confirmed; however, the effect was weaker than that of the WRI-4 expression vector.

Example 4

Suppression of WT117AA mRNA Expression by siRNA Expression Vector

Effects of the WRI-4 vector in suppressing WT117AA mRNA expression were examined by RT-PCR.

2 μg of the WRI-4 RNAi expression vector directed against the 17AA site of WT1, or an empty vector, was introduced into HT-1080 cells ($2 \times 10^4$ cells) by Lipofection using Fugene 6 (Roche). Cells were collected 96 hours after the introduction. The cells were then trypsinized and washed twice with PBS. Then, total RNA was extracted using Trizol, and cDNA was synthesized in the presence of MMLV reverse transcriptase using 2 μg of the total RNA as template and dT primer. Next, PCR was performed using forward primer 5'-gac ctg gaa tca gat gaa ctt ag-3' (SEQ ID NO: 7) and reverse primer 5'-gag aac ttt cgc tga caa gtt-3' (SEQ ID NO: 8), which are designed to sandwich the 17AA site of WT1, the PCR products were subjected to electrophoresis on an agarose gel, and expression of the WT1 17AA(+) and 17AA(−) mRNA was examined.

The results are shown in FIG. 2. Decrease of the 17AA(+) WT1 mRNA expression was observed in cells transfected with the WRI-4 expression vector.

Example 5

Construction of siRNA Vectors

Figure 3:
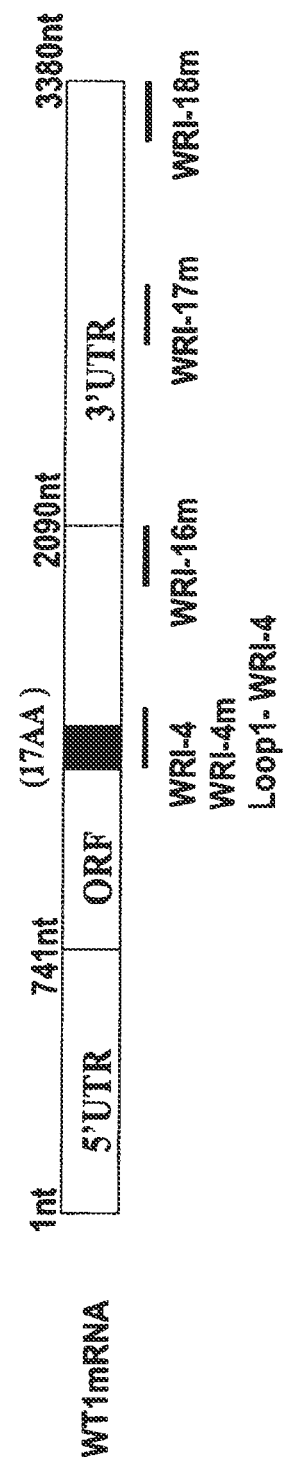
FIG. 3 shows the target sites of vector-based WT1 siRNAs.
Figure 4:
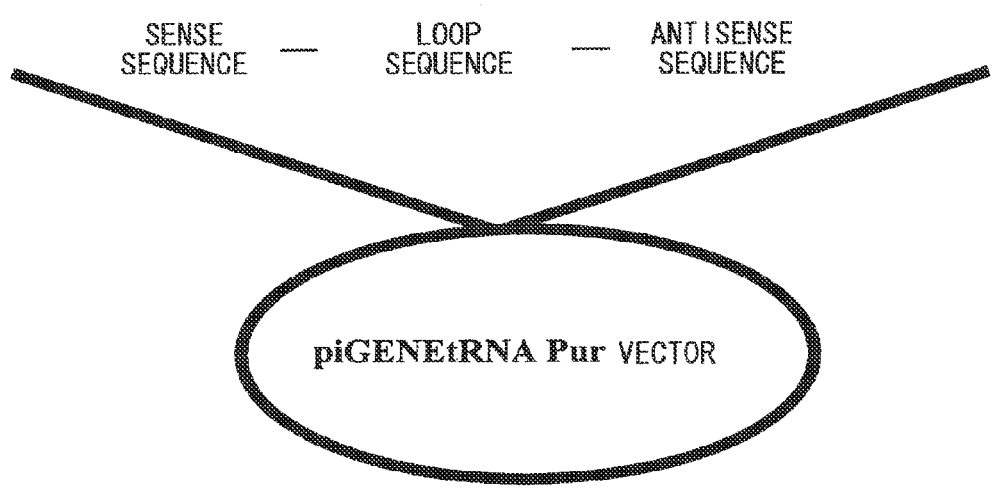
FIG. 4 shows the structure of vector-based WT1 siRNAs.

One type of an oligonucleotide whose sequence is specific to WT1 mRNA and comprises a loop 1 sequence (40 nt, SEQ ID NO: 18) (sense strand (30 nt)-loop 1 (40 nt, SEQ ID NO: 18)-antisense strand (30 nt)), and five types of an oligonucleotide whose sequence is specific to WT1 mRNA and comprises a loop 2 sequence (10 nt: the loop sequence of human pre-miR-23, SEQ ID NO: 19) (sense strand (30 nt)-loop 2 (10 nt, SEQ ID NO: 19)-antisense strand (30 nt)) were synthesized (Japan Bio Service). After annealing these oligonucleotides, they were inserted downstream of the tRNA$^{Val}$ promoter of the piGENEtRNA Pur Vector (Clonetech) to produce a total of six types of siRNA vectors, loop1-WRI-4 that transcribes dsRNA comprising loop1 (40 nt, SEQ ID NO: 18), and WRI-4, WRI-4m, WRI-16m, WRI-17m, and WRI-18m, which transcribe dsRNA comprising loop 2 (10 nt). Among them, those indicated with m are vectors carrying a sequence, into which mutations were inserted to the sense strand to increase the effect of vector-based WT1 siRNAs. The target site and sequence of each of the siRNA vectors are shown in FIG. 3, FIG. 4, and Table 1.

TABLE 1

| siRNA Vector | | Sequence$^a$ | SEQ ID NO | Loop$^b$ | Position in WT1 |
|---|---|---|---|---|---|
| loop2-WRI-4 | Target Sequence | AGCTCCAGCTCAGTGAAATGGACAGAAGGG | 9 | loop 1 | 1150-1179 |
|  | Sense sequence | AGCTCCAGCTCAGTGAAATGGACAGAAGGG | 10 |  |  |
| WRI-4 | Target Sequence | AGCTCCAGCTCAGTGAAATGGACAGAAGGG | 9 | loop 2 | 1150-1179 |
|  | Sense sequence | AGCTCCAGCTCAGTGAAATGGACAGAAGGG | 10 |  |  |
| WRI-4m | Target Sequence | AGCTCCAGCTCAGTGAAATGGACAGAAGGG | 9 | loop 2 | 1150-1179 |
|  | Sense sequence | AGCTCCAGCTT̲AGTGAA̲GTGG̲GTAGG̲AGGG | 11 |  |  |

TABLE 1-continued

| siRNA Vector | | Sequence[a] | SEQ ID NO | Loop[b] | Position in WT1 |
|---|---|---|---|---|---|
| WRI-16m | Target Sequence | AAACATGACCAAACTCCAGCTGGCGCTTTG | 12 | loop 2 | 1710-1739 |
| | Sense sequence | AAACATGACCAAACTCTAGTTGGTGCTTTG | 13 | | |
| WRI-17m | Target Sequence | AACCATGCTGGTATATGGCTTCAAGTTGTA | 14 | loop 2 | 2578-2607 |
| | Sense sequence | AACCATGCTGGTATATGGCTTTAGGTTGTG | 15 | | |
| WRI-18m | Target Sequence | AAGTACTAGATGCATCACTGGGTGTTGATC | 16 | loop 2 | 2906-2935 |
| | Sense sequence | AAGTACTAGATGCATCATTGGGTGTTGGTT | 17 | | |

[a]Underlines in the sense sequences indicate insertion of mutations.
[b]The sequence of loop 1 is AAAACTCGAGAAAAAAGGGAGCACAACCATCTGCATTTGAGAGG (SEQ ID NO: 18), and the sequence of loop 2 is CTTCCTGTCA (SEQ ID NO: 19).

Example 6

Suppression of WT1 Gene Expression by Vector-Based WT1 siRNA

Efficiency of suppression of WT1 gene expression in HT-1080 fibrosarcoma cells was examined for the six types of vector-based WT1 siRNAs targeting various sites in WT1 mRNA: loop 1-WRI-4, WRI-4, WRI-4m, WRI-16m, WRI-17m, and WRI-18m, and a mixture of WRI-4m, WRI-16m, WRI-17m, and WRI-18m (FIG. 3, FIG. 4, and Table 1).

HT-1080 cells were treated with the six vector-based WT1 siRNAs and a mock vector, respectively, and 72 hours later, the WT1 protein expression levels were analyzed by Western blotting.

Treatments with the siRNA vectors and mock vector were carried out in the following steps. Cells were plated onto a 6-well plate, and on the next day, the WT1-siRNA expression vectors and mock vector were transiently expressed by lipofection using FuGENE 6 (Roche). Three days later, the cells were trypsinized and the number of cells was counted. The WT1 protein expression level in these cells was analyzed by Western blotting.

Western blot analysis was carried out by the following steps. Cells transiently expressing the siRNA expression vectors and mock vector were dissolved in an SDS sample buffer, and proteins were separated by SDS-PAGE and then blotted onto a PVDF membrane. Color was developed using a BCIP-NBT kit with the anti-WT1 antibody C-19 (Santa Cruz Biotechnology), an anti-cytochrome C antibody (Pharmingen), or an anti-GAPDH antibody (Chemicon) as a primary antibody, and an ALP-conjugated anti-rabbit or anti-mouse antibody (Santa Cruz Biotechnology) as a second antibody.

Figure 5:
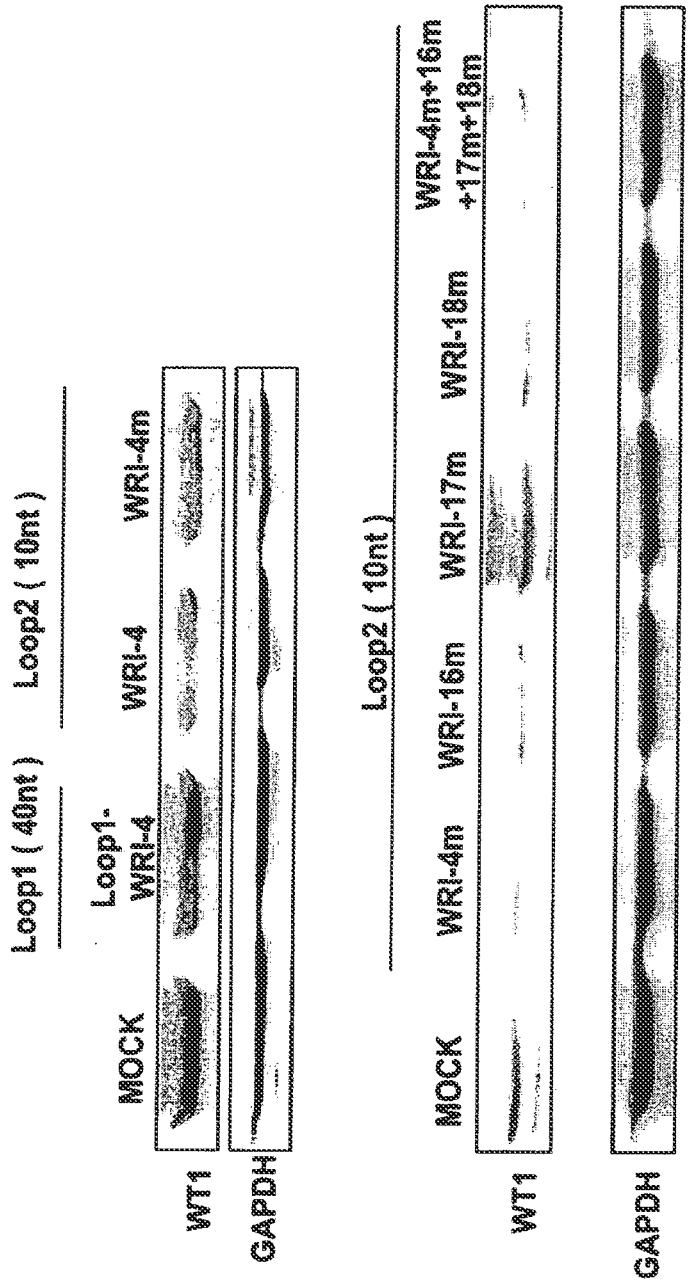
FIG. 5 shows photographs that indicate the suppression of WT1 protein expression by vector-based WT1 siRNAs.

Results of the Western blot analysis showed that expression of the WT1 protein is decreased by all of the WT1-targeting vector-based WT1 siRNAs. Herein, when treated with WRI-4, WRI-4m, WRI-16m, WRI-18m, and WRI-4m+16m+17m+18m, the protein expression level decreased to 10 to 20% in comparison with cells transfected with a mock vector; however, when treated with loop1-WRI-4 and WRI-17, the extent of decrease in WT1 protein expression was small (FIG. 5).

Example 7

WT1-Specific Growth Suppression of Tumor Cells by Vector-Based WT1 siRNA

Figure 6:
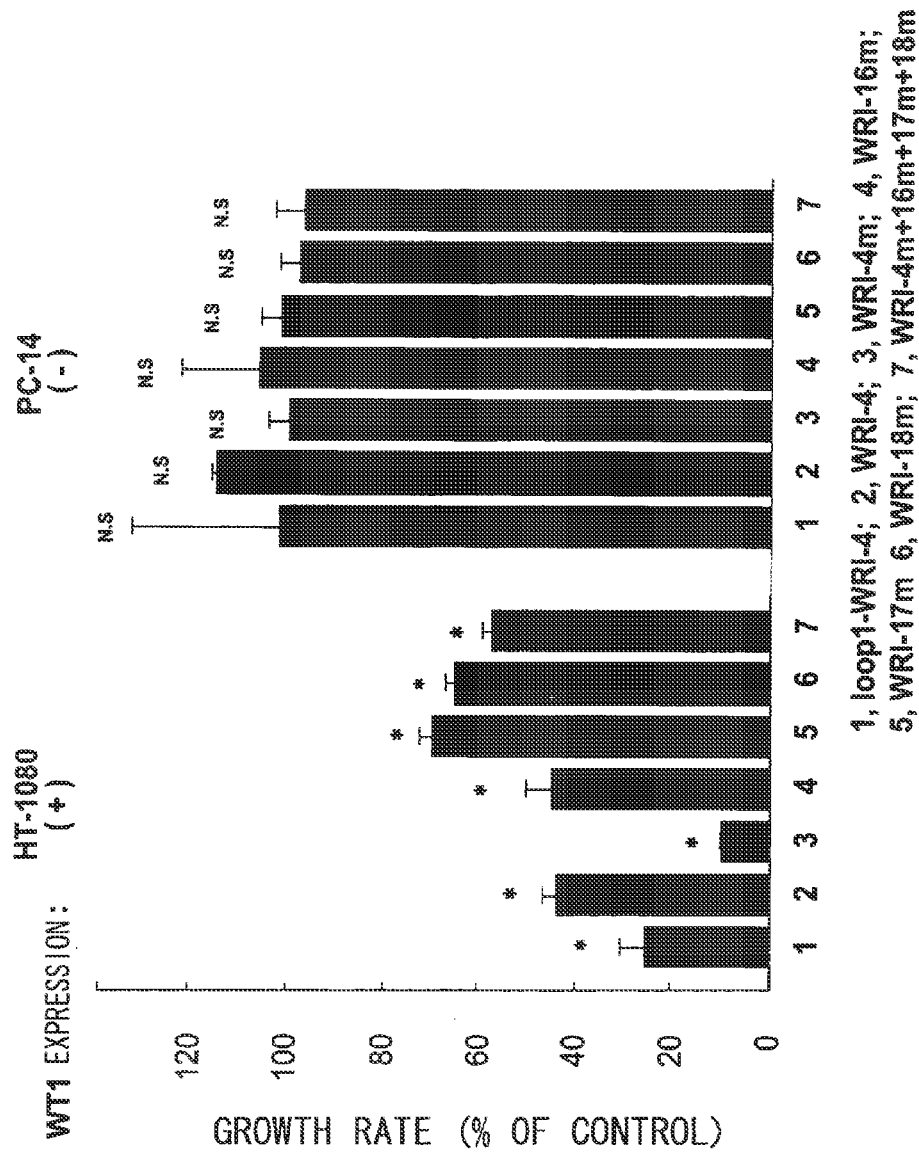
FIG. 6 shows suppression of cancer cell growth by vector-based WT1 siRNAs.

To analyze the effect of vector-based WT1 siRNAs on cell growth, the number of cells was counted 72 hours after introducing the six types of vector-based WT1 siRNAs, loop1-WRI-4, WRI-4, WRI-4m, WRI-16m, WRI-17m, and WRI-18m, and a mixture of WRI-4m, WRI-16m, WRI-17m, and WRI-18m, respectively. In HT-1080 fibrosarcoma cells (an WT1-expressing cell line), all of the WT1 siRNA treatments significantly suppressed cell growth compared to mock vector treatment. Among the WT1 siRNAs, WRI-4m suppressed growth by 90% or more. In contrast, in PC-14 lung cancer cells (a non-WT1-expressing cell line), cell growth was not suppressed by any of the six vector-based WT1 siRNA treatments (FIG. 6).

Furthermore, to investigate whether two types of vector-based WT1 siRNAs (WRI-4m and WRI-16m) can suppress the growth of various WT1-expressing cancer cells, these vectors were introduced into three WT1-expressing cell lines: AZ-521 gastric cancer cells, SW620 colon cancer cells, and HL-60 leukemia cells, and the number of cells were counted 72 hours later.

Figure 7:
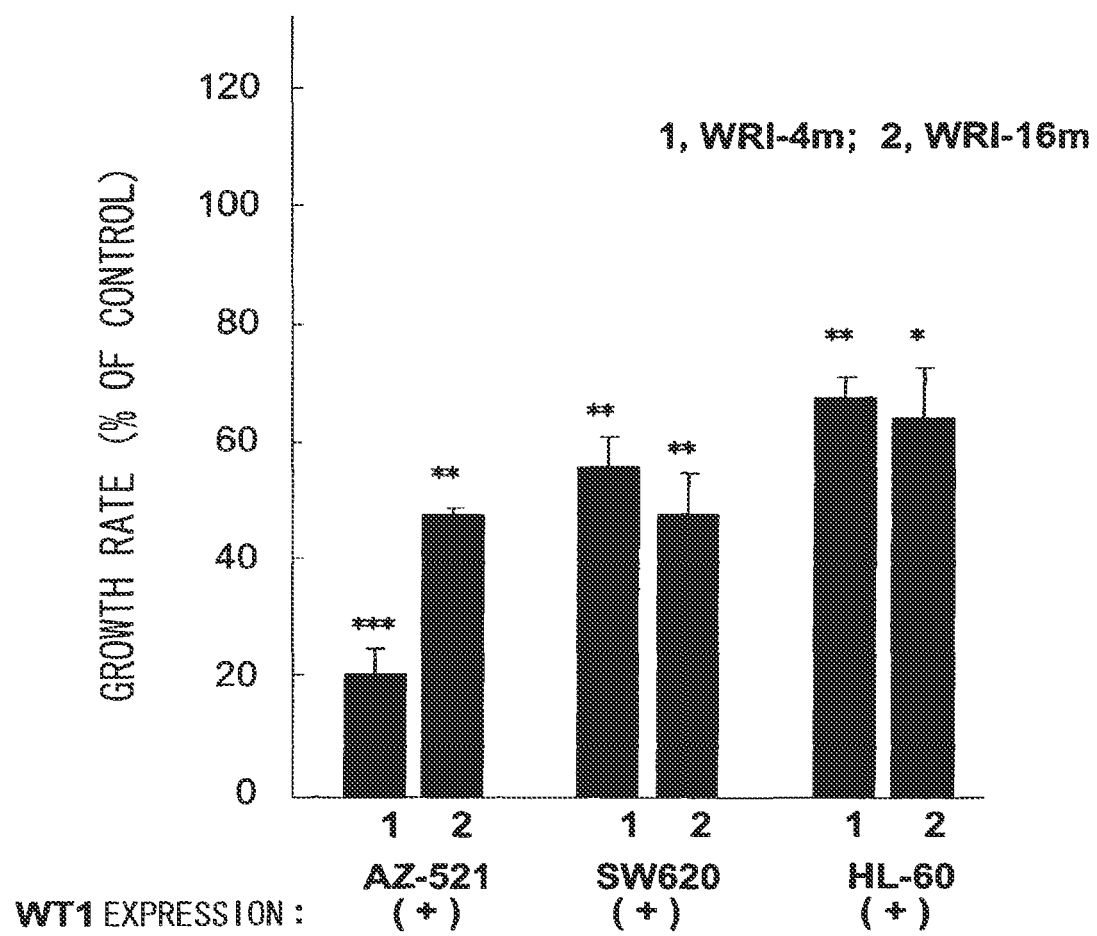
FIG. 7 shows suppression of cancer cell growth by vector-based WT1 siRNAs.

The results showed that in all three types of the WT1-expressing cancer cells, WRI-4m and WRI-16m treatments significantly suppressed growth compared to mock vector treatment (FIG. 7).

Example 8

Induction of Apoptosis by Vector-Based WT1 siRNA

To elucidate the mechanism of cancer cell growth suppression by vector-based WT1 siRNAs, induction of apoptosis in cells subjected to a vector-based WT1 siRNA treatment was analyzed. Two WT1-expressing cell lines HT-1080 and AZ-521, and a non-WT1-expressing cell line PC-14 were subjected to the WRI-4m treatment, double-stained with AnnexinV-FITC and PI, and then analyzed by flow cytometry.

Apoptosis analysis by flow cytometry was carried out by the following steps. First, to detect apoptosed cells, $1.0 \times 10^5$ cells were washed with PBS, and then the cells were stained by reaction with Annexin V-FITC and PI at room temperature for 15 minutes, using the MEBCYTO Apoptosis kit (Medical and Biological Laboratories Co., Ltd, Nagoya, Japan). Upon analysis of these cells using a FACScan flowcytometer (Becton Dickinson, San Jose, Calif.), Annexin V-FITC-positive cells were defined as apoptosed cells.

Figure 8:
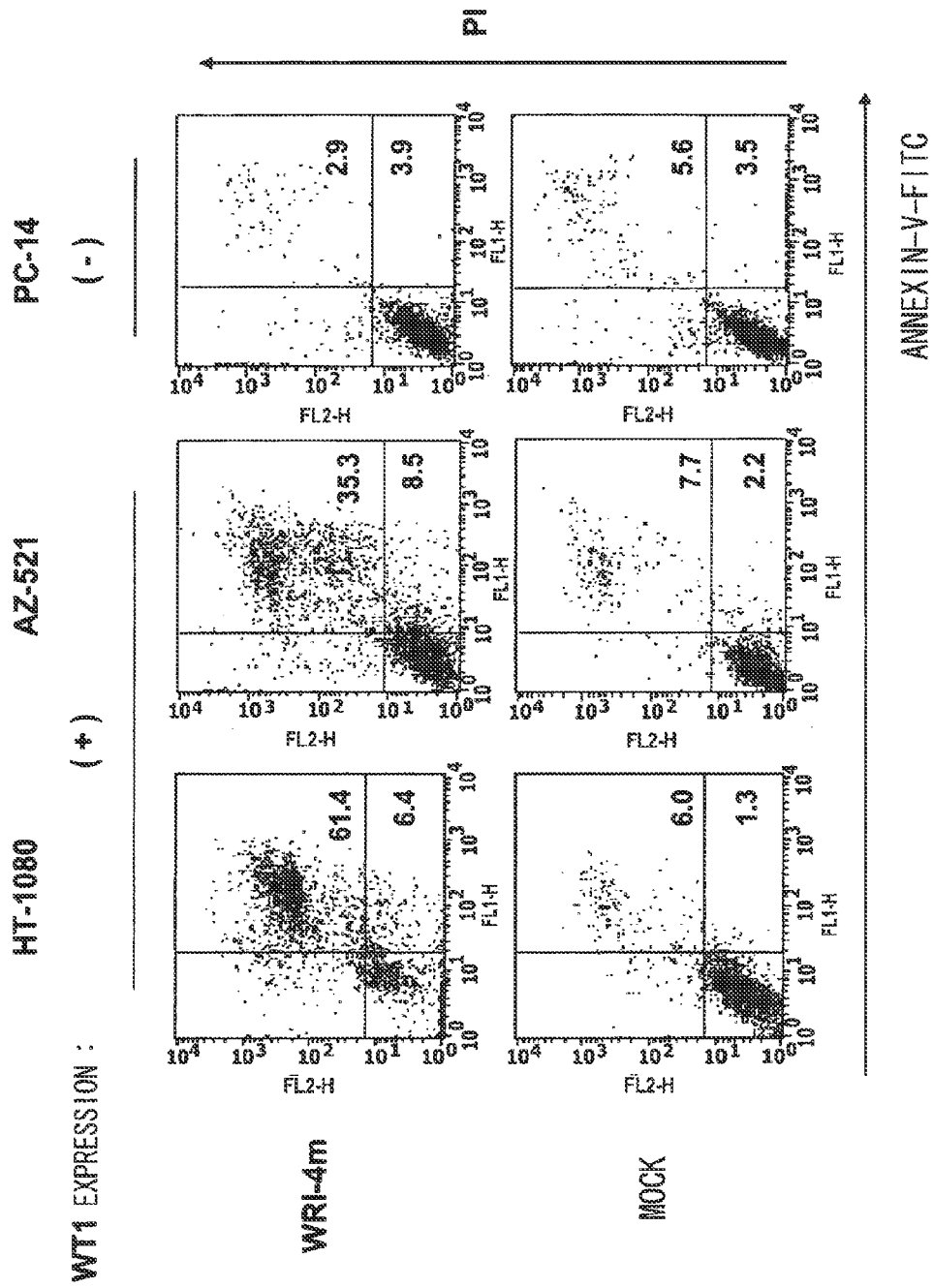
FIG. 8 shows the induction of apoptosis in cancer cells by a vector-based WT1 siRNA.
Figure 9:
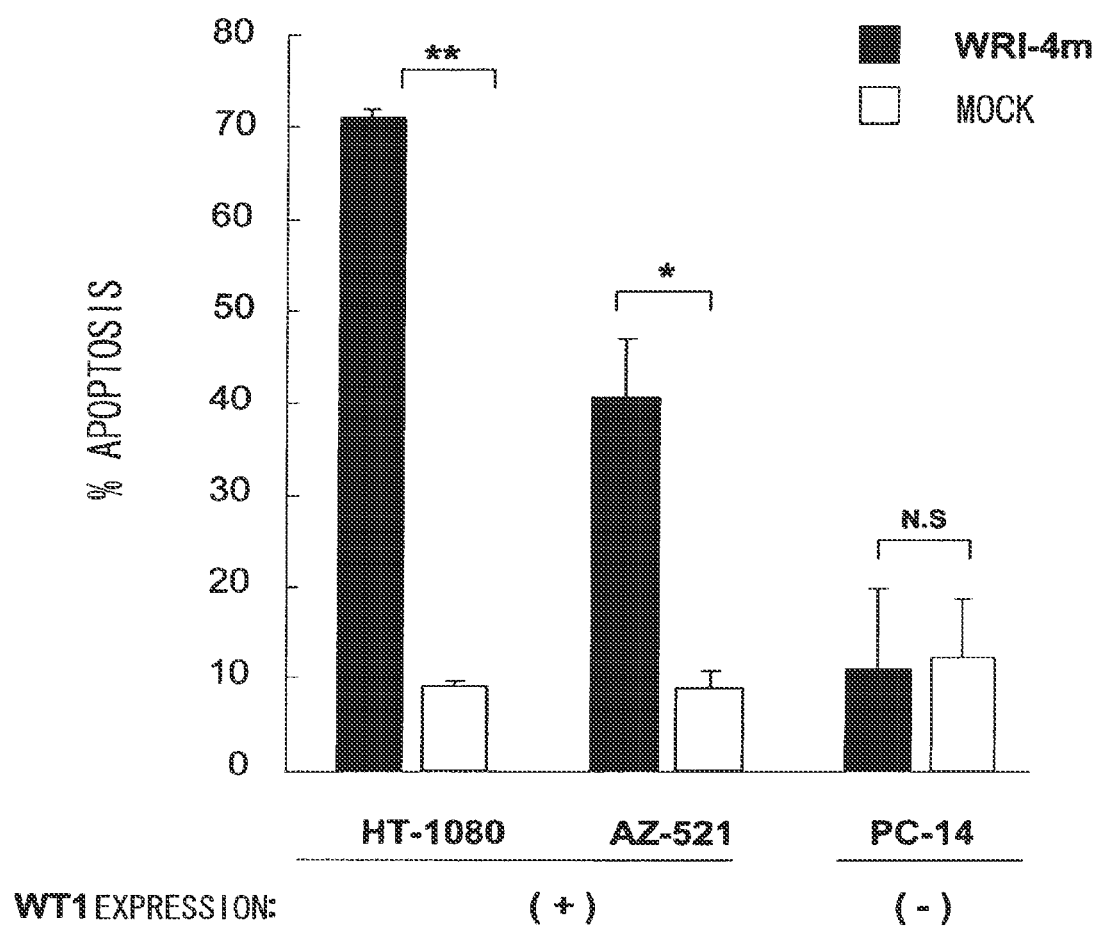
FIG. 9 shows the induction of apoptosis in cancer cells by a vector-based WT1 siRNA.

As a result, the WRI-4m treatment induced apoptosis in 71.1% and 40.6% of the WT1-expressing cell lines HT-1080 cells and AZ-521 cells, respectively. In contrast, in the non-WT1-expressing cell line PC-14, WRI-4m treatment did not induce apoptosis (FIGS. 8 and 9).

Example 9

Loss of Mitochondrial Membrane Potential by Vector-Based WT1 siRNA

To elucidate whether the vector-based WT1 siRNA-induced apoptosis takes place through a mitochondria-mediated pathway, the WT1-expressing cell line HT-1080 cells and the non-WT1-expressing cell line PC14 cells were both treated with WRI-4m and a mock vector respectively. 72 hours later, the state of mitochondrial membrane potential was analyzed by MitoLight staining followed by flow cytometry.

The change in mitochondrial membrane potential ($\Delta\Psi m$) due to apoptosis induction was analyzed using the MitoLight apoptosis detection kit (Chemicon). Cells after apoptosis induction were incubated at 37° C. in a buffer containing MitoLight (a mitochondria staining dye) for 15 minutes, and then analyzed on a FACScan FL2 channel.

Figure 10:
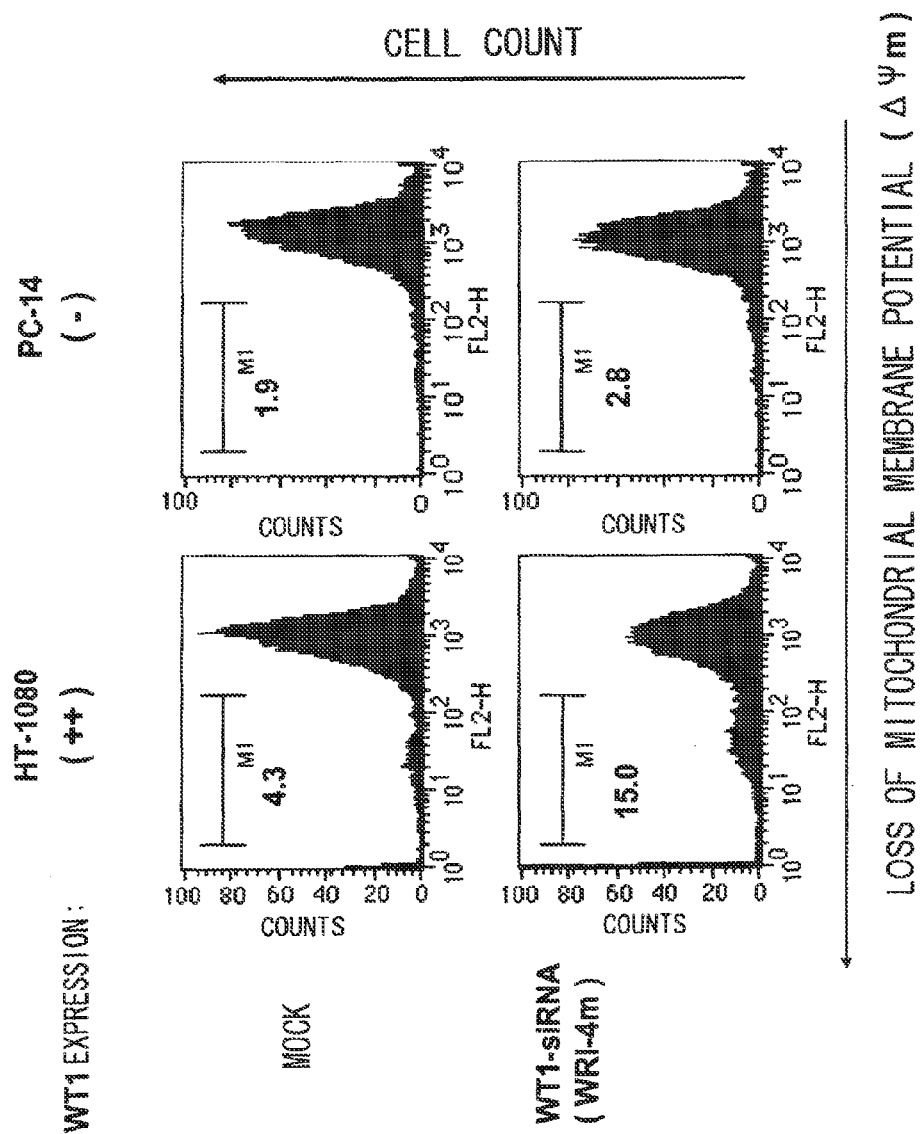
FIG. 10 shows the loss of mitochondrial membrane potential by a vector-based WT1 siRNA.
Figure 11:
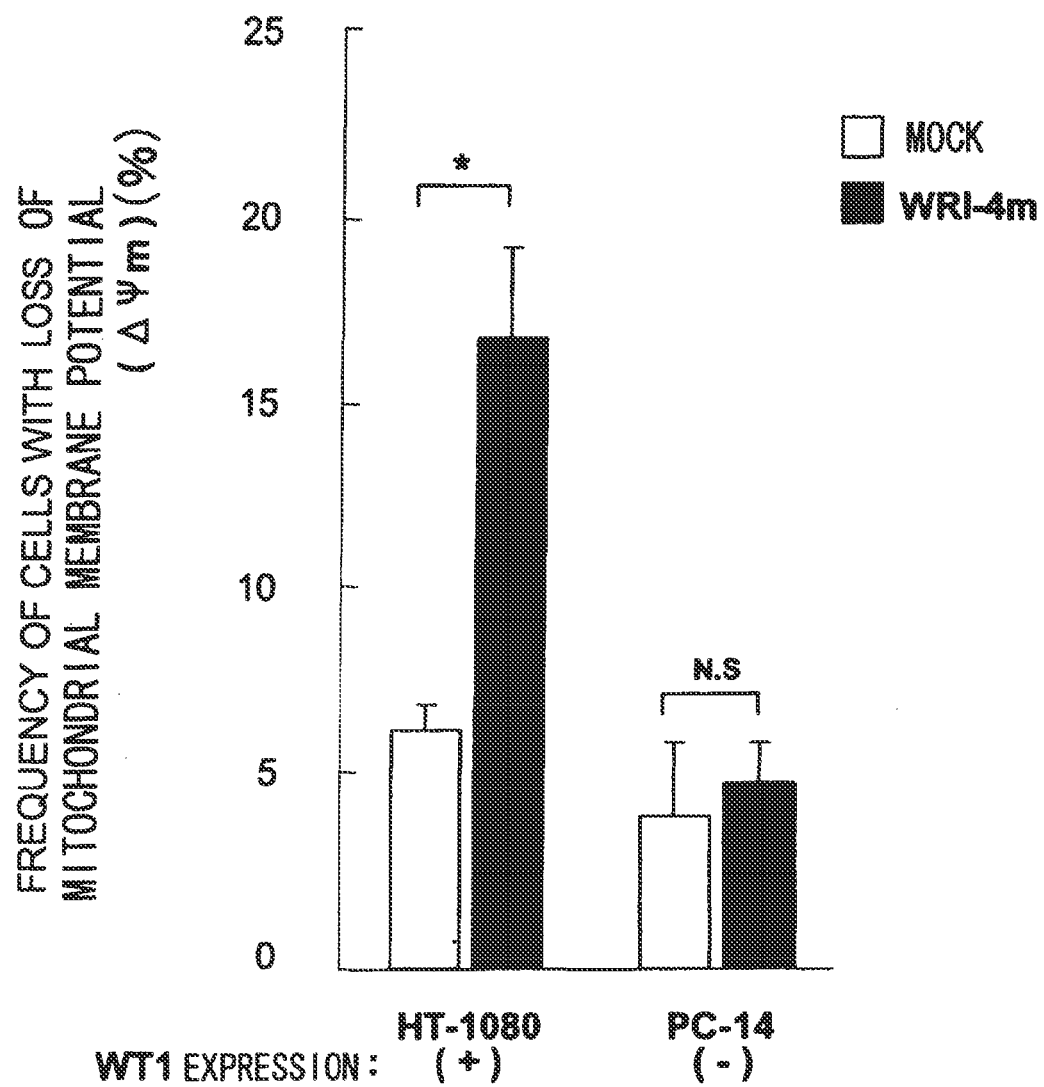
FIG. 11 shows the frequency of cells with loss of mitochondrial membrane potential by a vector-based WT1 siRNA.

As a result, compared to the mock vector treatment, the WRI-4m treatment significantly induced loss of the mitochondrial membrane potential in HT-1080 (a WT1-expressing cell line). However, the WRI-4m treatment did not induce loss of the mitochondrial membrane potential in the non-WT1-expressing cell line PC-14 (FIGS. 10 and 11). These results indicated that apoptosis induction by vector-based WT1 siRNA takes place through a mitochondria-mediated pathway.

Example 10

Enhancement of Cell Growth Suppression Through Combined Use of Vector-Based WT1 siRNA with Anti-Cancer Agents Most anticancer agents induce apoptosis in cancer cells through a mitochondria-mediated pathway. Therefore, the present inventors thought that the sensitivity of cancer cells to anticancer agents may be enhanced by using chemotherapeutic agents in combination with a vector-based WT1 siRNA that eliminates the mitochondrial membrane potential. Accordingly, cell growth suppression by anticancer agents doxorubicin and etoposide in cells treated with a vector-based WT1 siRNA (WRI-4m or WRI-16m) and untreated cells was analyzed.

Combined use of an siRNA vector with a chemotherapeutic agent or a death ligand, was carried out by the following steps. Cells were plated onto a 6-well plate, and on the next day, the vector-based WT1 siRNA and mock vector were transiently expressed by lipofection using FuGENE 6 (Roche), and 48 hours later, the cells were treated for another 24 hours with 25 µM etoposide (WAKO), 0.2 µM doxorubicin (Sigma), or 50 mg/mL of TNF-related apoptosis-inducing ligand (TRAIL) (Peprotech).

Figure 12:
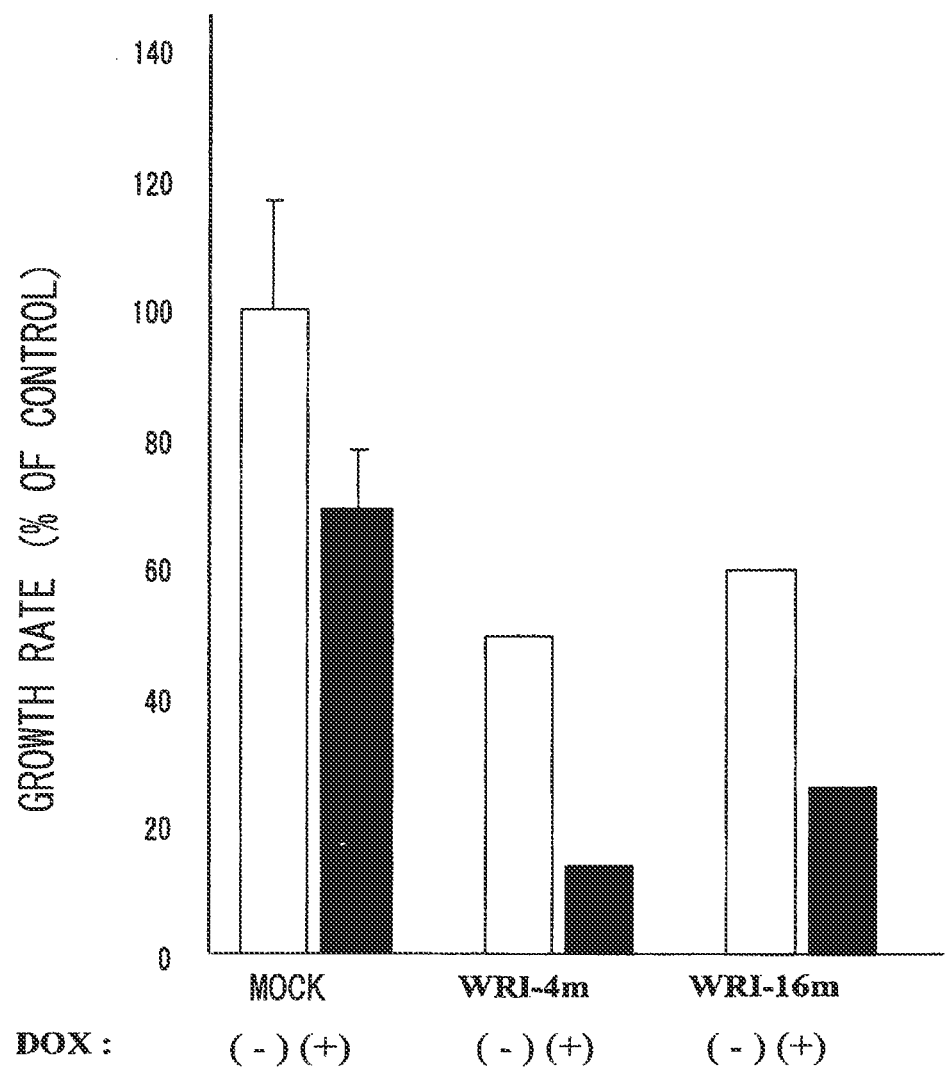
FIG. 12 shows the suppression of cancer cell growth by the combined use of a vector-based WT1 siRNA with anticancer agent doxorubicin.
Figure 13:
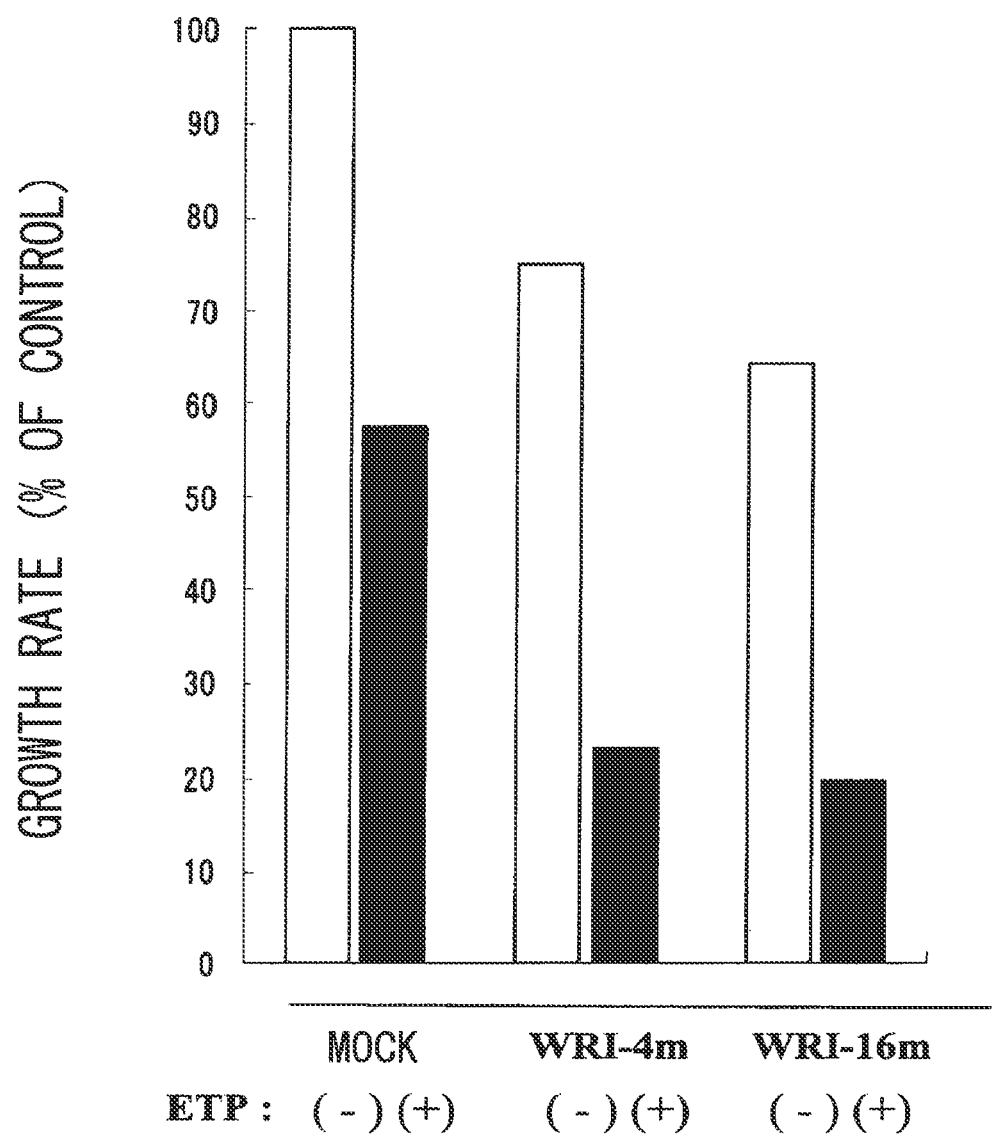
FIG. 13 shows the suppression of cancer cell growth by the combined use of a vector-based WT1 siRNA with anticancer agent etoposide.

The results showed that suppression of HT-1080 cell growth is greater when vector-based WT1 siRNA is used in combination with doxorubicin or etoposide than when only doxorubicin or etoposide is used (FIGS. 12 and 13).

Figure 14:
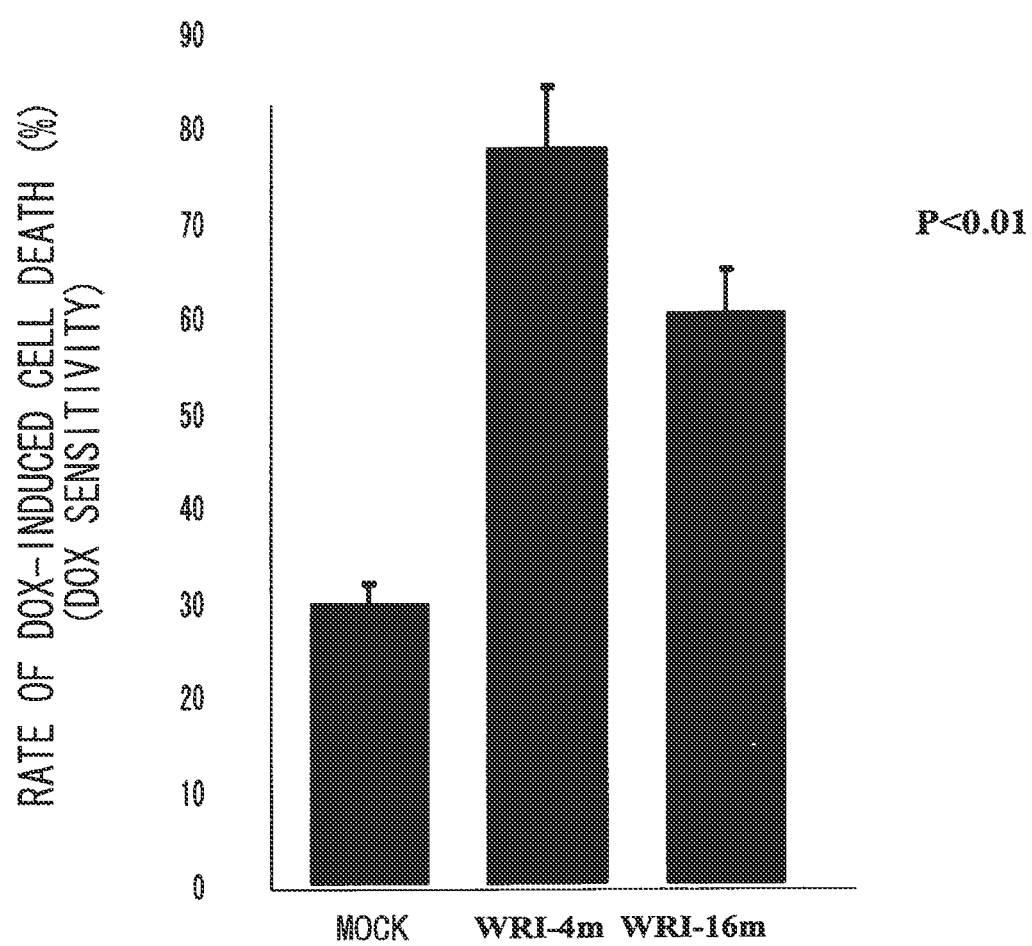
FIG. 14 shows enhancement of the doxorubicin sensitivity of cancer cells by vector-based WT1 siRNAs.
Figure 15:
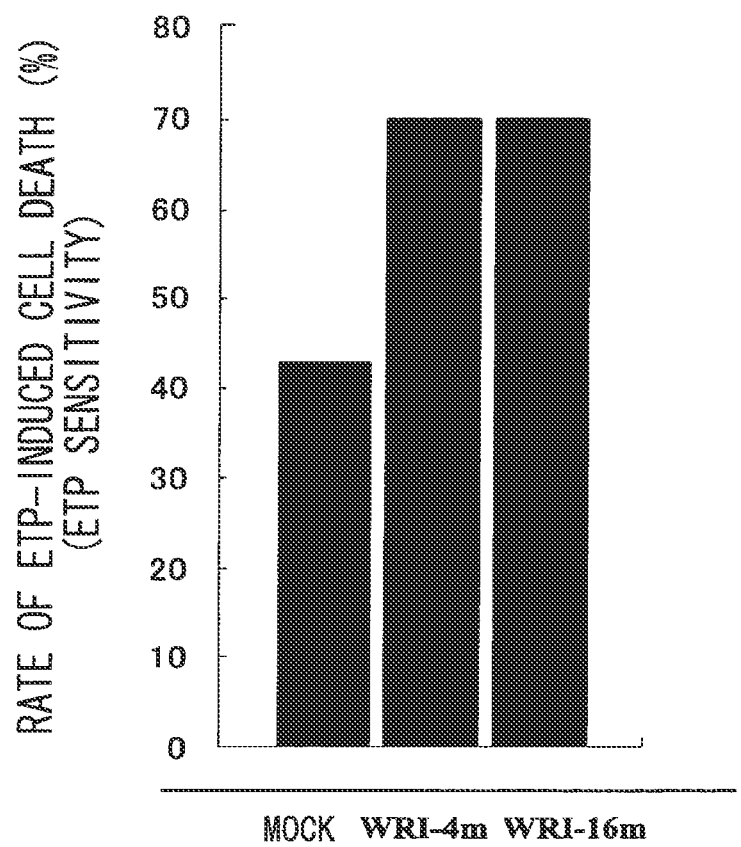
FIG. 15 shows enhancement of the etoposide sensitivity of cancer cells by vector-based WT1 siRNAs.

Furthermore, to analyze the cell sensitivity to anticancer agents after vector-based WT1 siRNA treatment, difference in the number of cells counted after combined treatment and after the vector treatment alone was calculated as a percentage relative to the number of cells counted after the vector treatment alone. The results showed that sensitivity to doxorubicin and etoposide is enhanced by vector-based WT1-siRNA treatment in HT-1080 cells, as indicated in FIGS. 14 and 15.

Example 11

Enhancing the Induction of Mitochondria-Mediated Apoptosis by Combined Use of Vector-Based WT1 siRNA with an Anticancer Agent To reveal that enhancement of cell growth suppression due to combined use of vector-based WT1-siRNA with an anticancer agent is caused by enhancing the induction of mitochondria-mediated apoptosis, the release of cytochrome c from mitochondria into cytoplasm which takes place after combined treatment of vector-based WT1-siRNA with doxorubicin or etoposide was analyzed.

The release of cytochrome c from mitochondria into cytoplasm was analyzed by the following steps. Cells were washed with PBS, dissolved in ice-cooled STE buffer (250 mM sucrose, 25 mM Tris, and 1 mM EDTA, pH6.8), and then centrifuged at 15,000 rpm for 15 minutes. The supernatant was mixed with an equal amount of 2× Laemmli's SDS sample buffer, and then stored at −20° C. until it was used in Western blot analysis.

Figure 16:
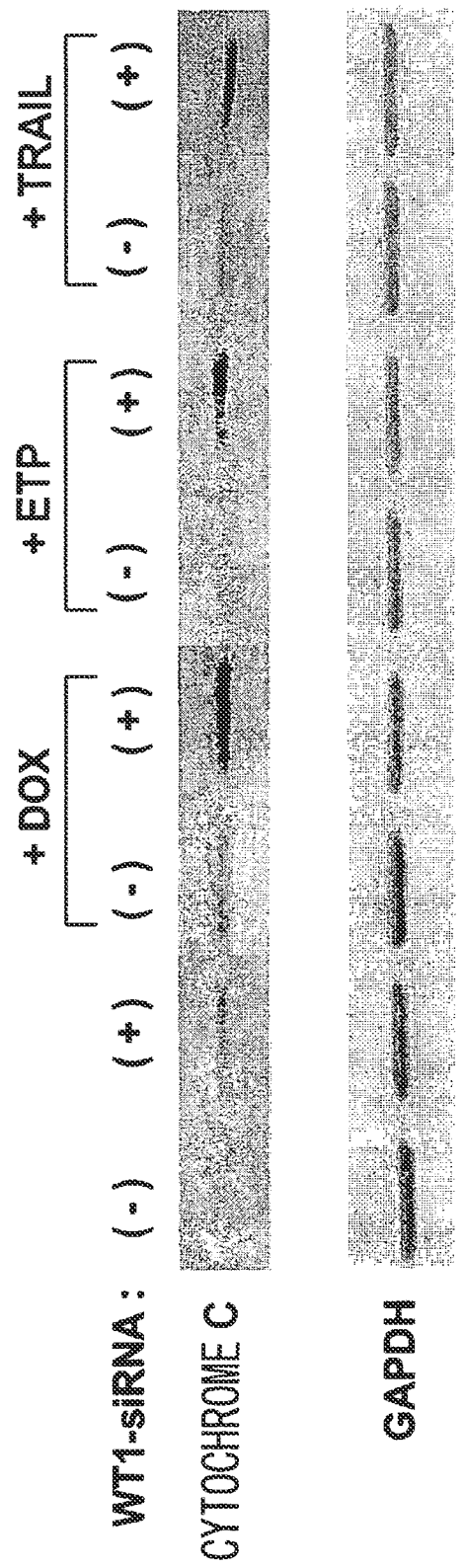
FIG. 16 is a photograph showing enhancement of the cytochrome c release in cancer cells by the combined use of a vector-based WT1 siRNA with anticancer agents.

The analysis results showed that the release of cytochrome c into cytoplasm is enhanced by combined treatment of WRI-4m with the respective agents, as shown in FIG. 16.

Figure 17:
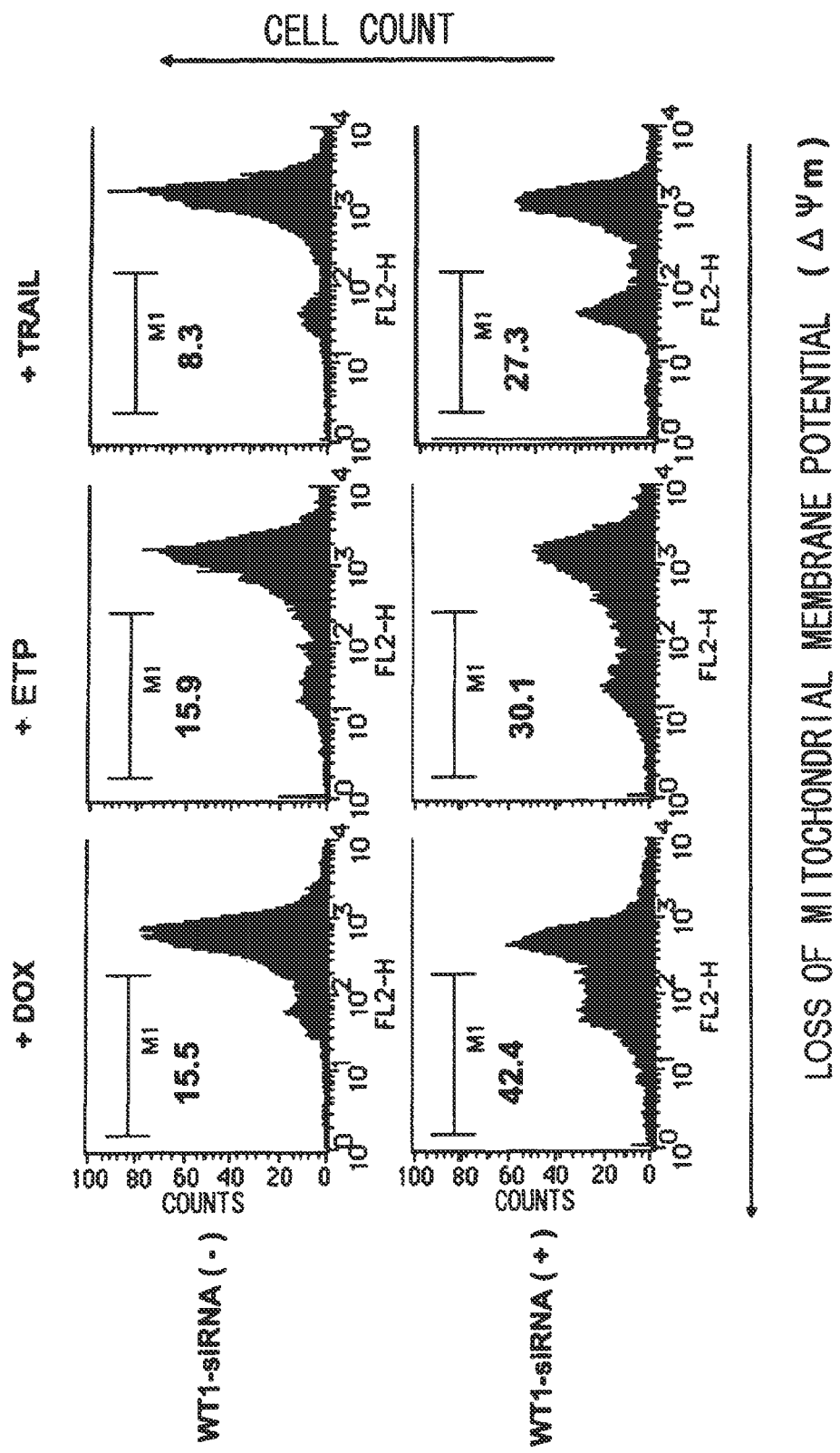
FIG. 17 shows enhancement of the loss of the potential in mitochondrial membrane in cancer cells by the combined use of a vector-based WT1 siRNA with anticancer agents.
Figure 18:
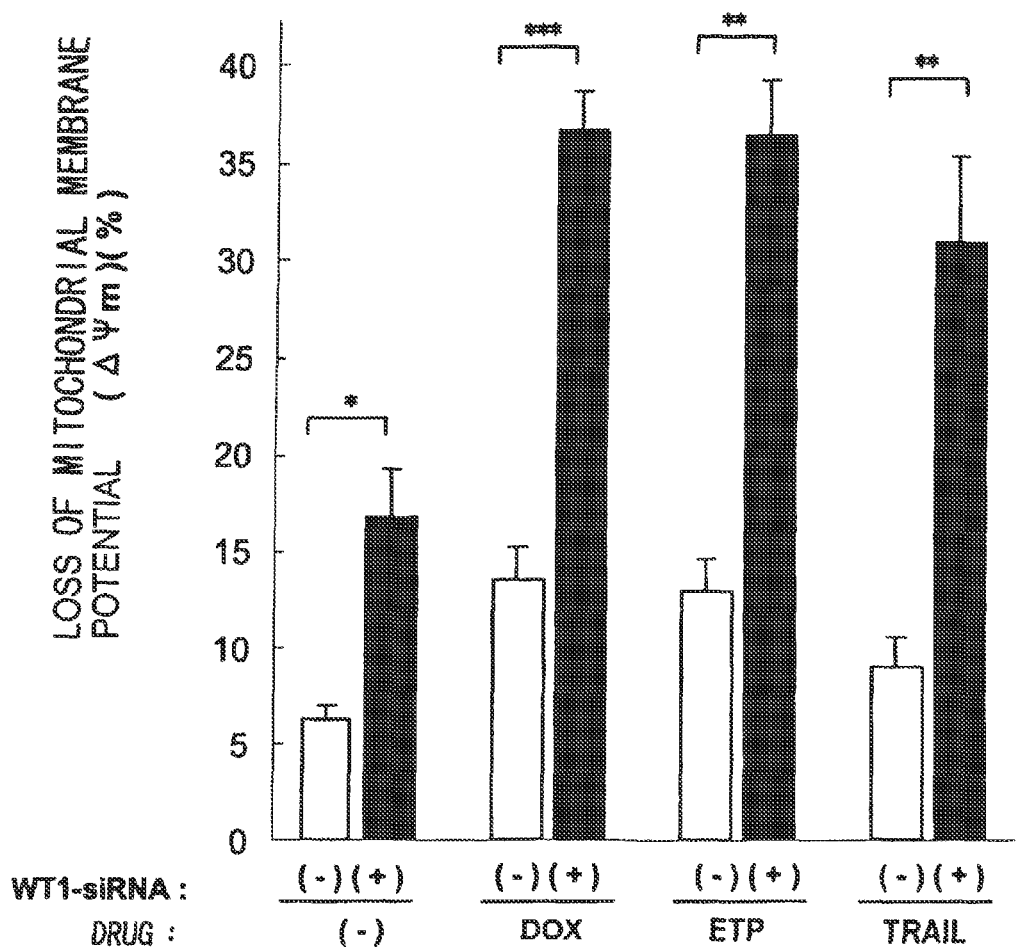
FIG. 18 shows enhancement of the loss of the potential in mitochondrial membrane in cancer cells by the combined use of a vector-based WT1 siRNA with anticancer agents.

Mitochondrial membrane potential after combined treatment using vector-based WT1 siRNA with doxorubicin, etoposide, and TRAIL, respectively, was evaluated by flow cytometry. Compared to treatment of an anticancer agent alone, combined treatment of WRI-4m with doxorubicin or etoposide significantly enhanced the loss of mitochondrial membrane potential (FIGS. 17 and 18).

When effects of the combined use of TRAIL, an attractive cancer-specific apoptosis-inducing agent, with a vector-based WT1 siRNA were analyzed, release of cytochrome c was enhanced (FIG. 16) and loss of mitochondrial membrane potential was enhanced (FIGS. 17 and 18) after the combined treatment, as with the combined use of a vector-based WT1 siRNA with doxorubicin or etoposide.

Industrial Applicability

The present invention provides siRNA that can efficiently suppress WT1 gene expression, and cell growth-suppressing agents comprising such siRNA as an active ingredient. It also provides cell death-inducing agents comprising such siRNA as an active ingredient, and agents that enhance the sensitivity of cancer cells to anticancer agents and cell death-inducing agents.

Since the WT1 gene is known to be highly expressed in cancer cells, the agents of the present invention are particularly useful as novel anticancer agents. Furthermore, since the agents of the present invention comprising siRNA as an active ingredient have functions of enhancing the effects of conventional anticancer agents, they are further expected to improve conventional anticancer drug therapy.

The invention claimed is:

1. A method of suppressing cell growth of cancer cells, the method comprising adding any one of (a) to (c) below to the cancer cells:
  (a) a double-stranded RNA consisting of (i) a first RNA complementary to a nucleotide sequence consisting of SEQ ID NO: 9, and (ii) a second RNA complementary to the first RNA, wherein either or both of the first RNA and the second RNA optionally further include a single-stranded overhang;
  (b) DNA comprising a sequence that is transcribed into the first RNA of (a) and a sequence that is transcribed into the second RNA of (a); or
  (c) a vector comprising DNA of (b).

2. The method of claim 1, wherein each single-stranded overhang, if present, is 1 to 8 bases in length.

3. The method of claim 1, wherein neither the first RNA nor the second RNA has a single-stranded overhang.

4. The method of claim 1, wherein the cancer cells are fibrosarcoma cells, colon cancer cells, leukemia cells, gastric cancer cells, lung cancer cells, breast cancer cells, squamous carcinoma cells, esophageal cancer cells, thyroid cancer cells, sarcoma cells, ovarian cancer cells, uterine cancer cells, kidney cancer cells, pancreatic cancer cells, or glioblastoma cells.

5. The method of claim 1, wherein the method induces death of the cancer cells.

6. The method of claim 1, wherein the method comprises adding the double-stranded RNA of (a) to the cancer cells.

7. The method of claim 1, wherein the method comprises adding the DNA of (b) to the cancer cells.

8. The method of claim 1, wherein the method comprises adding the vector of (c) to the cancer cells.

9. A method of suppressing cell growth of cancer cells, the method comprising adding any one of (a) to (c) below to the cancer cells:
  (a) a double-stranded RNA consisting of (i) a first RNA complementary to a nucleotide sequence consisting of SEQ ID NO: 11, and (ii) a second RNA complementary to the first RNA, wherein either or both of the first RNA and the second RNA optionally further include a single-stranded overhang;
  (b) DNA comprising a sequence that is transcribed into the first RNA of (a) and a sequence that is transcribed into the second RNA of (a); or
  (c) a vector comprising DNA of (b).

10. The method of claim 9, wherein each single-stranded overhang, if present, is 1 to 8 bases in length.

11. The method of claim 9, wherein neither the first RNA nor the second RNA has a single-stranded overhang.

12. The method of claim 9, wherein the cancer cells are fibrosarcoma cells, colon cancer cells, leukemia cells, gastric cancer cells, lung cancer cells, breast cancer cells, squamous carcinoma cells, esophageal cancer cells, thyroid cancer cells, sarcoma cells, ovarian cancer cells, uterine cancer cells, kidney cancer cells, pancreatic cancer cells, or glioblastoma cells.

13. The method of claim 9, wherein the method induces death of the cancer cells.

14. The method of claim 9, wherein the method comprises adding the double-stranded RNA of (a) to the cancer cells.

15. The method of claim 9, wherein the method comprises adding the DNA of (b) to the cancer cells.

16. The method of claim 9, wherein the method comprises adding the vector of (c) to the cancer cells.

17. A method of suppressing cell growth of cancer cells, the method comprising adding any one of (a) to (c) below to the cancer cells:
  (a) a double-stranded RNA consisting of (i) a first RNA complementary to a nucleotide sequence consisting of SEQ ID NO: 13, and (ii) a second RNA complementary to the first RNA, wherein either or both of the first RNA and the second RNA optionally further include a single-stranded overhang;
  (b) DNA comprising a sequence that is transcribed into the first RNA of (a) and a sequence that is transcribed into the second RNA of (a); or
  (c) a vector comprising DNA of (b).

18. The method of claim 17, wherein each single-stranded overhang, if present, is 1 to 8 bases in length.

19. The method of claim 17, wherein neither the first RNA nor the second RNA has a single-stranded overhang.

20. The method of claim 17, wherein the cancer cells are fibrosarcoma cells, colon cancer cells, leukemia cells, gastric cancer cells, lung cancer cells, breast cancer cells, squamous carcinoma cells, esophageal cancer cells, thyroid cancer cells, sarcoma cells, ovarian cancer cells, uterine cancer cells, kidney cancer cells, pancreatic cancer cells, or glioblastoma cells.

21. The method of claim 17, wherein the method induces death of the cancer cells.

22. The method of claim 17, wherein the method comprises adding the double-stranded RNA of (a) to the cancer cells.

23. The method of claim 17, wherein the method comprises adding the DNA of (b) to the cancer cells.

24. The method of claim 17, wherein the method comprises adding the vector of (c) to the cancer cells.

25. A method of suppressing cell growth of cancer cells, the method comprising adding any one of (a) to (c) below to the cancer cells:
  (a) a double-stranded RNA consisting of (i) a first RNA complementary to a nucleotide sequence consisting of SEQ ID NO: 15, and (ii) a second RNA complementary to the first RNA, wherein either or both of the first RNA and the second RNA optionally further include a single-stranded overhang;
  (b) DNA comprising a sequence that is transcribed into the first RNA of (a) and a sequence that is transcribed into the second RNA of (a); or
  (c) a vector comprising DNA of (b).

26. The method of claim 25, wherein each single-stranded overhang, if present, is 1 to 8 bases in length.

27. The method of claim 25, wherein neither the first RNA nor the second RNA has a single-stranded overhang.

28. The method of claim 25, wherein the cancer cells are fibrosarcoma cells, colon cancer cells, leukemia cells, gastric cancer cells, lung cancer cells, breast cancer cells, squamous carcinoma cells, esophageal cancer cells, thyroid cancer cells, sarcoma cells, ovarian cancer cells, uterine cancer cells, kidney cancer cells, pancreatic cancer cells, or glioblastoma cells.

29. The method of claim 25, wherein the method induces death of the cancer cells.

30. The method of claim 25, wherein the method comprises adding the double-stranded RNA of (a) to the cancer cells.

31. The method of claim 25, wherein the method comprises adding the DNA of (b) to the cancer cells.

32. The method of claim 25, wherein the method comprises adding the vector of (c) to the cancer cells.

33. A method of suppressing cell growth of cancer cells, the method comprising adding any one of (a) to (c) below to the cancer cells:
  (a) a double-stranded RNA consisting of (i) a first RNA complementary to a nucleotide sequence consisting of SEQ ID NO: 17, and (ii) a second RNA complementary to the first RNA, wherein either or both of the first RNA and the second RNA optionally further include a single-stranded overhang;
  (b) DNA comprising a sequence that is transcribed into the first RNA of (a) and a sequence that is transcribed into the second RNA of (a); or
  (c) a vector comprising DNA of (b).

34. The method of claim 33, wherein each single-stranded overhang, if present, is 1 to 8 bases in length.

35. The method of claim 33, wherein neither the first RNA nor the second RNA has a single-stranded overhang.

36. The method of claim 33, wherein the cancer cells are fibrosarcoma cells, colon cancer cells, leukemia cells, gastric cancer cells, lung cancer cells, breast cancer cells, squamous carcinoma cells, esophageal cancer cells, thyroid cancer cells, sarcoma cells, ovarian cancer cells, uterine cancer cells, kidney cancer cells, pancreatic cancer cells, or glioblastoma cells.

37. The method of claim 33, wherein the method induces death of the cancer cells.

38. The method of claim 33, wherein the method comprises adding the double-stranded RNA of (a) to the cancer cells.

39. The method of claim 33, wherein the method comprises adding the DNA of (b) to the cancer cells.

40. The method of claim 33, wherein the method comprises adding the vector of (c) to the cancer cells.

\* \* \* \* \*

SEQUENCE LISTING

<160> NUMBER OF SEQ ID NOS: 23

<210> SEQ ID NO 1
<211> LENGTH: 30
<212> TYPE: RNA

-continued

```
<213> ORGANISM: Artificial Sequence
<220> FEATURE:
<223> OTHER INFORMATION: An artificially synthesized RNA sequence

<400> SEQUENCE: 1
agcuccagcu cagugaaaug gacagaaggg                                     30

<210> SEQ ID NO 2
<211> LENGTH: 30
<212> TYPE: RNA
<213> ORGANISM: Artificial Sequence
<220> FEATURE:
<223> OTHER INFORMATION: An artificially synthesized RNA sequence

<400> SEQUENCE: 2
cccuucuguc cauuucacug agcuggagcu                                     30

<210> SEQ ID NO 3
<211> LENGTH: 96
<212> TYPE: DNA
<213> ORGANISM: Artificial Sequence
<220> FEATURE:
<223> OTHER INFORMATION: An artificially synthesized DNA sequence

<400> SEQUENCE: 3
cccttctgtc catttcactg agctggagct aaaactcgag aaaaagctcc agctcagtga    60
aatggacaga agggggtacc ccggatatct tttttt                              96

<210> SEQ ID NO 4
<211> LENGTH: 30
<212> TYPE: DNA
<213> ORGANISM: Artificial Sequence
<220> FEATURE:
<223> OTHER INFORMATION: An artificially synthesized DNA sequence

<400> SEQUENCE: 4
aaggtggctc ctaagttcat ctgattccag                                     30

<210> SEQ ID NO 5
<211> LENGTH: 30
<212> TYPE: DNA
<213> ORGANISM: Artificial Sequence
<220> FEATURE:
<223> OTHER INFORMATION: An artificially synthesized DNA sequence

<400> SEQUENCE: 5
ctggaatcag atgaacttag gagccacctt                                     30

<210> SEQ ID NO 6
<211> LENGTH: 3030
<212> TYPE: DNA
<213> ORGANISM: Homo sapiens

<400> SEQUENCE: 6
ggggtaagga gttcaaggca gcgcccacac ccggggggctc tccgcaaccc gaccgcctgt   60
ccgctccccc acttcccgcc ctccctccca cctactcatt cacccaccca cccacccaga  120
gccgggacgg cagcccaggc gcccgggccc cgccgtctcc tcgccgcgat cctggacttc  180
ctcttgctgc aggacccggc ttccacgtgt gtcccggagc cggcgtctca gcacacgctc  240
cgctccgggc ctgggtgcct acagcagcca gagcagcagg gagtccggga cccgggcggc  300
atctggccca gttaggcgc cgccgaggcc agcgctgaac gtctccaggg ccggaggagc  360
cgcggggcgt ccgggtctga gccgcagcaa atgggctccg acgtgcggga cctgaacgcg  420
```

```
ctgctgcccg ccgtcccctc cctgggtggc ggcggcggct gtgccctgcc tgtgagcggc      480
gcggcgcagt gggcgccggt gctggacttt gcgcccccgg gcgcttcggc ttacgggtcg      540
ttgggcggcc ccgcgccgcc accggctccg ccgccacccc cgccgccgcc gcctcactcc      600
ttcatcaaac aggagccgag ctgggcggc gcggagccgc acgaggagca gtgcctgagc       660
gccttcactg tccactttc cggccagttc actggcacag ccggagcctg tcgctacggg       720
cccttcggtc ctcctccgcc cagccaggcg tcatccggcc aggccaggat gtttcctaac     780
gcgccctacc tgcccagctg cctcgagagc cagcccgcta ttcgcaatca gggttacagc     840
acggtcacct tcgacgggac gcccagctac ggtcacacgc cctcgcacca tgcggcgcag     900
ttccccaacc actcattcaa gcatgaggat cccatgggcc agcagggctc gctgggtgag     960
cagcagtact cggtgccgcc cccggtctat ggctgccaca cccccaccga cagctgcacc     1020
ggcagccagg ctttgctgct gaggacgccc tacagcagtg acaatttata ccaaatgaca     1080
tcccagcttg aatgcatgac ctggaatcag atgaacttag gagccacctt aaagggagtt     1140
gctgctggga gctccagctc agtgaaatgg acagaagggc agagcaacca cagcacaggg     1200
tacgagagcg ataaccacac aacgcccatc ctctgcggag cccaatacag aatacacacg     1260
cacggtgtct tcagaggcat tcaggatgtg cgacgtgtgc ctggagtagc cccgactctt     1320
gtacggtcgg catctgagac cagtgagaaa cgccccttca tgtgtgctta cccaggctgc     1380
aataagagat attttaagct gtcccactta cagatgcaca gcaggaagca cactggtgag     1440
aaaccatacc agtgtgactt caaggactgt gaacgaaggt tttctcgttc agaccagctc     1500
aaaagacacc aaaggagaca tacaggtgtg aaaccattcc agtgtaaaac ttgtcagcga     1560
aagttctccc ggtccgacca cctgaagacc cacaccagga ctcatacagg taaaacaagt     1620
gaaaagccct tcagctgtcg gtggccaagt tgtcagaaaa agtttgcccg gtcagatgaa     1680
ttagtccgcc atcacaacat gcatcagaga aacatgacca aactccagct ggcgctttga     1740
ggggtctccc tcggggaccg ttcagtgtcc caggcagcac agtgtgtgaa ctgctttcaa     1800
gtctgactct ccactcctcc tcactaaaaa ggaaacttca gttgatcttc ttcatccaac     1860
ttccaagaca agataccggt gcttctggaa actaccaggt gtgcctggaa gagttggtct     1920
ctgccctgcc tacttttagt tgactcacag gccctggaga agcagctaac aatgtctggt     1980
tagttaaaag cccattgcca tttggtgtgg attttctact gtaagaagag ccatagctga     2040
tcatgtcccc ctgaccccttc ccttctttt ttatgctcgt tttcgctggg gatggaatta     2100
ttgtaccatt ttctatcatg gaatatttat aggccagggc atgtgtatgt gtctgctaat     2160
gtaaactttg tcatggtttc catttactaa cagcaacagc aagaaataaa tcagagagca     2220
aggcatcggg ggtgaatctt gtctaacatt cccgaggtca gccaggctgc taacctggaa     2280
agcaggatgt agttctgcca ggcaacttttt aaagctcatg catttcaagc agctgaagaa     2340
aaaatcagaa ctaaccagta cctctgtata gaaatctaaa agaattttac cattcagtta     2400
attcaatgtg aacactggca cactgctctt aagaaactat gaagatctga attttttttg     2460
tgtatgtttt tgactctttt gagtggtaat catatgtgtc tttatagatg tacatacctc     2520
cttgcacaaa tggaggggaa ttcatttttca tcactgggag tgtccttagt gtataaaaac     2580
catgctggta tatggcttca agttgtaaaa atgaaagtga ctttaaaaga aaataggggga     2640 tggtccagga tctccactga taagactgtt tttaagtaac ttaaggacct ttgggtctac     2700
aagtatatgt gaaaaaaatg agacttactg ggtgaggaaa tccattgttt aaagatggtc     2760
gtgtgtgtgt gtgtgtgtgt gtgtgtgttg tgttgtgttt tgttttttaa gggagggaat     2820
```

-continued

```
ttattattta ccgttgcttg aaattactgt gtaaatatat gtctgataat gatttgctct    2880
ttgacaacta aaattaggac tgtataagta ctagatgcat cactgggtgt tgatcttaca    2940
agatattgat gataacactt aaaattgtaa cctgcatttt tcactttgct ctcaattaaa    3000
gtctattcaa aaggaaaaaa aaaaaaaaaa                                      3030

<210> SEQ ID NO 7
<211> LENGTH: 23
<212> TYPE: DNA
<213> ORGANISM: Artificial Sequence
<220> FEATURE:
<223> OTHER INFORMATION: An artificially synthesized primer sequence

<400> SEQUENCE: 7
gacctggaat cagatgaact tag                                              23

<210> SEQ ID NO 8
<211> LENGTH: 21
<212> TYPE: DNA
<213> ORGANISM: Artificial Sequence
<220> FEATURE:
<223> OTHER INFORMATION: An artificially synthesized primer sequence

<400> SEQUENCE: 8
gagaactttc gctgacaagt t                                                21

<210> SEQ ID NO 9
<211> LENGTH: 30
<212> TYPE: DNA
<213> ORGANISM: Homo sapiens

<400> SEQUENCE: 9
agctccagct cagtgaaatg gacagaaggg                                       30

<210> SEQ ID NO 10
<211> LENGTH: 30
<212> TYPE: DNA
<213> ORGANISM: Artificial Sequence
<220> FEATURE:
<223> OTHER INFORMATION: An artificially synthesized DNA sequence

<400> SEQUENCE: 10
agctccagct cagtgaaatg gacagaaggg                                       30

<210> SEQ ID NO 11
<211> LENGTH: 30
<212> TYPE: DNA
<213> ORGANISM: Artificial Sequence
<220> FEATURE:
<223> OTHER INFORMATION: an artificially synthesized DNA sequence

<400> SEQUENCE: 11
agctccagct tagtgaagtg ggtaggaggg                                       30

<210> SEQ ID NO 12
<211> LENGTH: 30
<212> TYPE: DNA
<213> ORGANISM: Homo sapiens

<400> SEQUENCE: 12
aaacatgacc aaactccagc tggcgctttg                                       30

<210> SEQ ID NO 13
<211> LENGTH: 30
<212> TYPE: DNA
```

<213> ORGANISM: Artificial Sequence
<220> FEATURE:
<223> OTHER INFORMATION: an artificially synthesized DNA sequence

<400> SEQUENCE: 13
aaacatgacc aaactctagt tggtgctttg          30

<210> SEQ ID NO 14
<211> LENGTH: 30
<212> TYPE: DNA
<213> ORGANISM: Homo sapiens

<400> SEQUENCE: 14
aaccatgctg gtatatggct tcaagttgta          30

<210> SEQ ID NO 15
<211> LENGTH: 30
<212> TYPE: DNA
<213> ORGANISM: Artificial Sequence
<220> FEATURE:
<223> OTHER INFORMATION: an artificially synthesized DNA sequence

<400> SEQUENCE: 15
aaccatgctg gtatatggct ttaggttgtg          30

<210> SEQ ID NO 16
<211> LENGTH: 30
<212> TYPE: DNA
<213> ORGANISM: Homo sapiens

<400> SEQUENCE: 16
aagtactaga tgcatcactg ggtgttgatc          30

<210> SEQ ID NO 17
<211> LENGTH: 30
<212> TYPE: DNA
<213> ORGANISM: Artificial Sequence
<220> FEATURE:
<223> OTHER INFORMATION: an artificially synthesized DNA sequence

<400> SEQUENCE: 17
aagtactaga tgcatcattg ggtgttggtt          30

<210> SEQ ID NO 18
<211> LENGTH: 44
<212> TYPE: DNA
<213> ORGANISM: Artificial Sequence
<220> FEATURE:
<223> OTHER INFORMATION: an artificially synthesized DNA sequence

<400> SEQUENCE: 18
aaaactcgag aaaaaaggga gcacaaccat ctgcatttga gagg          44

<210> SEQ ID NO 19
<211> LENGTH: 10
<212> TYPE: DNA
<213> ORGANISM: Artificial Sequence
<220> FEATURE:
<223> OTHER INFORMATION: an artificially synthesized DNA sequence

<400> SEQUENCE: 19
cttcctgtca          10

<210> SEQ ID NO 20
<211> LENGTH: 30
<212> TYPE: DNA

```
<213> ORGANISM: Artificial Sequence
<220> FEATURE:
<223> OTHER INFORMATION: an artificially synthesized DNA sequence

<400> SEQUENCE: 20
cccttctgtc catttcactg agctggagct                                    30

<210> SEQ ID NO 21
<211> LENGTH: 14
<212> TYPE: DNA
<213> ORGANISM: Artificial Sequence
<220> FEATURE:
<223> OTHER INFORMATION: an artificially synthesized DNA sequence

<400> SEQUENCE: 21
aaaactcgag aaaa                                                     14

<210> SEQ ID NO 22
<211> LENGTH: 30
<212> TYPE: DNA
<213> ORGANISM: Artificial Sequence
<220> FEATURE:
<223> OTHER INFORMATION: an artificially synthesized DNA sequence

<400> SEQUENCE: 22
agctccagct cagtgaaatg gacagaaggg                                    30

<210> SEQ ID NO 23
<211> LENGTH: 22
<212> TYPE: DNA
<213> ORGANISM: Artificial Sequence
<220> FEATURE:
<223> OTHER INFORMATION: an artificially synthesized DNA sequence

<400> SEQUENCE: 23 ggtacccgg atatcttttt tt                                             22
```